United States Patent
Hasegawa et al.

(10) Patent No.: US 9,568,992 B2
(45) Date of Patent: Feb. 14, 2017

(54) MEDICAL MANIPULATOR

(71) Applicant: OLYMPUS CORPORATION, Tokyo (JP)

(72) Inventors: Mitsuaki Hasegawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 67 days.

(21) Appl. No.: 14/168,525

(22) Filed: Jan. 30, 2014

(65) Prior Publication Data
US 2014/0148817 A1 May 29, 2014

Related U.S. Application Data

(63) Continuation of application No. PCT/JP2012/070416, filed on Aug. 3, 2012.
(Continued)

(30) Foreign Application Priority Data

Jul. 13, 2012 (JP) .................................. 2012-157788

(51) Int. Cl.
*A61B 19/00* (2006.01)
*G06F 3/01* (2006.01)
(Continued)

(52) U.S. Cl.
CPC ................. *G06F 3/01* (2013.01); *A61B 17/29* (2013.01); *A61B 17/32002* (2013.01);
(Continued)

(58) Field of Classification Search
CPC ........ A61B 19/20; A61B 19/201; A61B 19/22
See application file for complete search history.

(56) References Cited

U.S. PATENT DOCUMENTS 3,139,990 A    7/1964   Jelatis et al.
3,923,166 A   12/1975   Fletcher et al.
(Continued)

FOREIGN PATENT DOCUMENTS

| CN | 101027010 A | 8/2007 |
| CN | 101167658 A | 4/2008 |
| CN | 101426412 A | 5/2009 |
| DE | 10 2008 041 867 A1 | 3/2010 |
| EP | 0 677 278 A1 | 10/1995 |
| EP | 1 728 475 A2 | 12/2006 |
| EP | 2 092 875 A1 | 8/2009 |

(Continued)

OTHER PUBLICATIONS

U.S. Office Action dated Apr. 9, 2015 received in related U.S. Appl. No. 14/169,675.
(Continued)

*Primary Examiner* — Melanie Tyson
(74) *Attorney, Agent, or Firm* — Scully, Scott, Murphy & Presser, PC

(57) ABSTRACT

A medical manipulator including a base section at which a support surface is formed, a movable part movably supported on the support surface, when a reference direction parallel to the support surface is defined, between a distal end position, which is a distal end side in the reference direction with respect to the base section, and a proximal end position, which is a proximal end side in the reference direction, a positioning mechanism configured to position the movable part at the distal end position with respect to the base section, a holding section movably supported in the reference direction with respect to the movable part and configured to detachably hold a proximal end portion of a treatment tool, and a driving unit configured to move the holding section in the reference direction with respect to the movable part.

11 Claims, 12 Drawing Sheets

Related U.S. Application Data

(60) Provisional application No. 61/515,203, filed on Aug. 4, 2011.

(51) Int. Cl.
*A61B 17/29* (2006.01)
*A61B 17/32* (2006.01)
*A61B 18/14* (2006.01)
*A61B 19/08* (2006.01)
*B25J 13/02* (2006.01)
*A61B 17/068* (2006.01)
*A61B 19/10* (2006.01)
*A61B 17/00* (2006.01)

(52) U.S. Cl.
CPC ........ *A61B 18/1402* (2013.01); *A61B 19/081* (2013.01); *A61B 19/22* (2013.01); *A61B 19/2203* (2013.01); *A61B 19/26* (2013.01); *A61B 19/44* (2013.01); *B25J 13/02* (2013.01); *A61B 17/068* (2013.01); *A61B 19/10* (2013.01); *A61B 19/5244* (2013.01); *A61B 19/56* (2013.01); *A61B 2017/00119* (2013.01); *A61B 2017/00477* (2013.01); *A61B 2017/00482* (2013.01); *A61B 2019/2223* (2013.01); *A61B 2019/2269* (2013.01); *A61B 2019/2292* (2013.01); *A61B 2019/2296* (2013.01); *A61B 2019/465* (2013.01); *A61B 2019/467* (2013.01); *A61B 2019/4815* (2013.01); *A61B 2019/4868* (2013.01); *A61B 2019/4873* (2013.01); *A61B 2019/5255* (2013.01); *A61B 2019/5289* (2013.01); *Y10S 901/08* (2013.01); *Y10S 901/09* (2013.01); *Y10S 901/30* (2013.01); *Y10T 29/49826* (2015.01); *Y10T 74/18056* (2015.01)

(56) References Cited

U.S. PATENT DOCUMENTS

| | | |
|---|---|---|
| 4,672,281 A | 6/1987 | Yagusic et al. |
| 4,830,569 A | 5/1989 | Jannborg |
| 4,872,803 A | 10/1989 | Asakawa |
| 5,214,969 A | 6/1993 | Adkins et al. |
| 5,603,723 A | 2/1997 | Aranyi et al. |
| 5,632,432 A | 5/1997 | Schulze et al. |
| 5,649,956 A | 7/1997 | Jensen et al. |
| 5,656,903 A | 8/1997 | Shui et al. |
| 5,712,543 A | 1/1998 | Sjostrom |
| 5,760,530 A | 6/1998 | Kolesar |
| 5,762,458 A | 6/1998 | Wang et al. |
| 5,784,542 A | 7/1998 | Ohm et al. |
| 5,817,119 A | 10/1998 | Klieman et al. |
| 5,836,869 A | 11/1998 | Kudo et al. |
| 5,855,583 A | 1/1999 | Wang et al. |
| 5,871,493 A | 2/1999 | Sjostrom et al. |
| 5,876,325 A | 3/1999 | Mizuno et al. |
| 6,007,550 A | 12/1999 | Wang et al. |
| 6,063,095 A | 5/2000 | Wang et al. |
| 6,082,797 A | 7/2000 | Antonette |
| 6,090,122 A | 7/2000 | Sjostrom et al. |
| 6,102,850 A | 8/2000 | Wang et al. |
| 6,132,368 A | 10/2000 | Cooper |
| 6,132,441 A | 10/2000 | Grace |
| 6,206,903 B1 | 3/2001 | Ramans |
| 6,246,200 B1 | 6/2001 | Blumenkranz et al. |
| 6,328,752 B1 | 12/2001 | Sjostrom et al. |
| 6,346,072 B1 | 2/2002 | Cooper |
| 6,430,473 B1 | 8/2002 | Lee et al. |
| 6,436,107 B1 | 8/2002 | Wang et al. |
| 6,441,577 B2 | 8/2002 | Blumenkranz et al. |
| 6,557,558 B1 | 5/2003 | Tajima et al. |
| 6,574,355 B2 | 6/2003 | Green |
| 6,587,750 B2 | 7/2003 | Gerbi et al. |
| 6,602,185 B1 | 8/2003 | Uchikubo |
| 6,645,196 B1 | 11/2003 | Nixon et al. |
| 6,666,876 B2 | 12/2003 | Kawai et al. |
| 6,676,684 B1 | 1/2004 | Morley et al. |
| 6,685,698 B2 | 2/2004 | Morley et al. |
| 6,699,177 B1 | 3/2004 | Wang et al. |
| 6,746,443 B1 | 6/2004 | Morley et al. |
| 6,783,524 B2 | 8/2004 | Anderson et al. |
| 6,786,896 B1 | 9/2004 | Madhani et al. |
| 6,853,879 B2 | 2/2005 | Sunaoshi |
| 6,866,671 B2 | 3/2005 | Tierney et al. |
| 6,905,460 B2 | 6/2005 | Wang et al. |
| 6,913,613 B2 | 7/2005 | Schwarz et al. |
| 7,083,571 B2 | 8/2006 | Wang et al. |
| 7,101,363 B2 | 9/2006 | Nishizawa et al. |
| 7,107,124 B2 | 9/2006 | Green |
| 7,118,582 B1 | 10/2006 | Wang et al. |
| 7,273,488 B2 | 9/2007 | Nakamura et al. |
| 7,295,893 B2 | 11/2007 | Sunaoshi |
| 7,313,464 B1 | 12/2007 | Perreault et al. |
| 7,331,967 B2 | 2/2008 | Lee et al. |
| 7,357,774 B2 | 4/2008 | Cooper |
| 7,373,219 B2 | 5/2008 | Nowlin et al. |
| 7,422,592 B2 | 9/2008 | Morley et al. |
| 7,476,237 B2 | 1/2009 | Taniguchi et al. |
| 7,549,998 B2 | 6/2009 | Braun |
| 7,594,912 B2 | 9/2009 | Cooper et al. |
| 7,608,083 B2 | 10/2009 | Lee et al. |
| 7,654,431 B2 | 2/2010 | Hueil et al. |
| 7,666,191 B2 | 2/2010 | Orban, III et al. |
| 7,674,255 B2 | 3/2010 | Braun |
| 7,695,481 B2 | 4/2010 | Wang et al. |
| 7,699,835 B2 | 4/2010 | Lee et al. |
| 7,699,855 B2 | 4/2010 | Anderson et al. |
| 7,778,733 B2 | 8/2010 | Nowlin et al. |
| 7,819,884 B2 | 10/2010 | Lee et al. |
| 7,819,885 B2 | 10/2010 | Cooper |
| 7,862,579 B2 | 1/2011 | Ortiz et al. |
| 7,865,266 B2 | 1/2011 | Moll et al. |
| 7,955,321 B2 | 6/2011 | Kishi et al. |
| 8,105,320 B2 | 1/2012 | Manzo |
| 8,155,479 B2 | 4/2012 | Hoffman et al. |
| 8,267,958 B2 | 9/2012 | Braun |
| 8,350,806 B2 | 1/2013 | Nagasaka et al. |
| 8,423,186 B2 | 4/2013 | Itkowitz et al. |
| 8,460,277 B2 | 6/2013 | Suarez et al. |
| 8,496,647 B2 | 7/2013 | Blumenkranz et al. |
| 8,540,748 B2 | 9/2013 | Murphy et al. |
| 8,744,137 B2 | 6/2014 | Sakai et al. |
| 8,845,681 B2 | 9/2014 | Grace |
| 8,876,858 B2 | 11/2014 | Braun |
| 8,888,789 B2 | 11/2014 | Prisco et al. |
| 8,903,549 B2 | 12/2014 | Itkowitz et al. |
| 8,906,002 B2 | 12/2014 | Kishi et al. |
| 9,039,681 B2 | 5/2015 | Wang et al. |
| 9,283,675 B2 | 3/2016 | Hager et al. |
| 9,308,009 B2 | 4/2016 | Madan et al. |
| 9,308,646 B2 | 4/2016 | Lim et al. |
| 2001/0021859 A1 | 9/2001 | Kawai et al. |
| 2001/0055062 A1 | 12/2001 | Shioda et al. |
| 2002/0072736 A1 | 6/2002 | Tierney et al. |
| 2002/0091374 A1 | 7/2002 | Cooper |
| 2002/0128552 A1 | 9/2002 | Nowlin et al. |
| 2003/0033024 A1 | 2/2003 | Sunaoshi |
| 2003/0060927 A1 | 3/2003 | Gerbi et al. |
| 2003/0069471 A1 | 4/2003 | Nakanishi et al. |
| 2003/0083648 A1 | 5/2003 | Wang et al. |
| 2003/0100817 A1 | 5/2003 | Wang et al. |
| 2003/0216723 A1 | 11/2003 | Shinmura et al. |
| 2004/0049205 A1 | 3/2004 | Lee et al. |
| 2004/0092912 A1 | 5/2004 | Jinno et al. |
| 2004/0111113 A1 | 6/2004 | Nakamura et al. |
| 2004/0140787 A1 | 7/2004 | Okamoto et al. |
| 2004/0186345 A1 | 9/2004 | Yang et al. |
| 2004/0186624 A1 | 9/2004 | Oda et al. |
| 2004/0243147 A1 | 12/2004 | Lipow |
| 2004/0246469 A1 | 12/2004 | Hirose |
| 2005/0020876 A1 | 1/2005 | Shioda et al. |

(56) References Cited

U.S. PATENT DOCUMENTS

| | | |
|---|---|---|
| 2005/0021050 A1 | 1/2005 | Cooper |
| 2005/0033117 A1 | 2/2005 | Ozaki et al. |
| 2005/0125027 A1 | 6/2005 | Knodel et al. |
| 2005/0149003 A1 | 7/2005 | Tierney et al. |
| 2005/0228365 A1 | 10/2005 | Wang et al. |
| 2005/0273086 A1 | 12/2005 | Green et al. |
| 2006/0052664 A1 | 3/2006 | Julian et al. |
| 2006/0074408 A1 | 4/2006 | Jinno et al. |
| 2006/0079865 A1 | 4/2006 | Jinno et al. |
| 2006/0079866 A1 | 4/2006 | Jinno et al. |
| 2006/0087746 A1 | 4/2006 | Lipow |
| 2006/0116973 A1 | 6/2006 | Okamoto et al. |
| 2006/0149162 A1* | 7/2006 | Daw ............... A61B 5/061 600/564 |
| 2006/0155262 A1 | 7/2006 | Kishi et al. |
| 2006/0161138 A1 | 7/2006 | Orban, III et al. |
| 2006/0190031 A1 | 8/2006 | Wales et al. |
| 2006/0235436 A1 | 10/2006 | Anderson et al. |
| 2007/0012135 A1 | 1/2007 | Tierney et al. |
| 2007/0089557 A1 | 4/2007 | Solomon et al. |
| 2007/0119274 A1 | 5/2007 | Devengenzo et al. |
| 2007/0137372 A1 | 6/2007 | Devengenzo et al. |
| 2007/0138992 A1 | 6/2007 | Prisco et al. |
| 2007/0142823 A1 | 6/2007 | Prisco et al. |
| 2007/0142825 A1 | 6/2007 | Prisco et al. |
| 2007/0156122 A1 | 7/2007 | Cooper |
| 2007/0167679 A1 | 7/2007 | Miyamoto et al. |
| 2007/0167680 A1 | 7/2007 | Miyamoto et al. |
| 2007/0173689 A1 | 7/2007 | Ozaki et al. |
| 2007/0197896 A1 | 8/2007 | Moll et al. |
| 2007/0208375 A1 | 9/2007 | Nishizawa et al. |
| 2007/0219668 A1 | 9/2007 | Takahashi et al. |
| 2007/0225550 A1 | 9/2007 | Gattani et al. |
| 2007/0249897 A1 | 10/2007 | Miyamoto et al. |
| 2007/0265638 A1 | 11/2007 | Lipow et al. |
| 2008/0015611 A1 | 1/2008 | Jinno et al. |
| 2008/0033240 A1 | 2/2008 | Hoffman et al. |
| 2008/0046122 A1 | 2/2008 | Manzo et al. |
| 2008/0051631 A1 | 2/2008 | Dejima et al. |
| 2008/0059131 A1 | 3/2008 | Tokita et al. |
| 2008/0103524 A1 | 5/2008 | Grace |
| 2008/0140088 A1 | 6/2008 | Orban, III |
| 2008/0147091 A1 | 6/2008 | Cooper |
| 2008/0177285 A1 | 7/2008 | Brock et al. |
| 2008/0204425 A1 | 8/2008 | Nagasaka et al. |
| 2008/0215065 A1 | 9/2008 | Wang et al. |
| 2008/0228196 A1 | 9/2008 | Wang et al. |
| 2008/0234866 A1 | 9/2008 | Kishi et al. |
| 2008/0243142 A1 | 10/2008 | Gildenberg |
| 2008/0262654 A1 | 10/2008 | Omori et al. |
| 2008/0287735 A1 | 11/2008 | Takemoto et al. |
| 2008/0312668 A1 | 12/2008 | Grace |
| 2009/0018700 A1 | 1/2009 | Okamoto et al. |
| 2009/0022262 A1 | 1/2009 | Ohishi |
| 2009/0030273 A1 | 1/2009 | Murakami |
| 2009/0034820 A1 | 2/2009 | Sugiyama |
| 2009/0036736 A1 | 2/2009 | Dejima et al. |
| 2009/0036902 A1 | 2/2009 | DiMaio et al. |
| 2009/0046146 A1 | 2/2009 | Hoyt |
| 2009/0057369 A1 | 3/2009 | Smith et al. |
| 2009/0088634 A1 | 4/2009 | Zhao et al. |
| 2009/0088773 A1 | 4/2009 | Zhao et al. |
| 2009/0088897 A1 | 4/2009 | Zhao et al. |
| 2009/0132088 A1 | 5/2009 | Taitler |
| 2009/0163948 A1 | 6/2009 | Sunaoshi et al. |
| 2009/0171147 A1 | 7/2009 | Lee et al. |
| 2009/0182193 A1 | 7/2009 | Whitman et al. |
| 2009/0193299 A1 | 7/2009 | Sekiguchi et al. |
| 2009/0204911 A1 | 8/2009 | Sekiguchi et al. |
| 2009/0247877 A1 | 10/2009 | Tanaka et al. |
| 2009/0281378 A1* | 11/2009 | Banju ............... A61B 1/00133 600/106 |
| 2009/0326318 A1 | 12/2009 | Tognaccini et al. |
| 2010/0010673 A1 | 1/2010 | Wang et al. |
| 2010/0013812 A1 | 1/2010 | Gu et al. |
| 2010/0087835 A1 | 4/2010 | Blumenkranz et al. |
| 2010/0160728 A1 | 6/2010 | Yoshie |
| 2010/0163057 A1 | 7/2010 | Anderson et al. |
| 2010/0174293 A1 | 7/2010 | Orban, III et al. |
| 2010/0217284 A1 | 8/2010 | Grace |
| 2010/0217528 A1 | 8/2010 | Sato et al. |
| 2010/0225209 A1 | 9/2010 | Goldberg et al. |
| 2010/0228264 A1 | 9/2010 | Robinson et al. |
| 2010/0228265 A1 | 9/2010 | Prisco |
| 2010/0234857 A1 | 9/2010 | Itkowitz et al. |
| 2010/0274087 A1 | 10/2010 | Diolaiti et al. |
| 2010/0291520 A1 | 11/2010 | Kurenov et al. |
| 2010/0317965 A1 | 12/2010 | Itkowitz et al. |
| 2010/0318099 A1 | 12/2010 | Itkowitz et al. |
| 2010/0318101 A1 | 12/2010 | Choi |
| 2010/0332031 A1 | 12/2010 | Itkowitz et al. |
| 2011/0015650 A1 | 1/2011 | Choi et al. |
| 2011/0050852 A1 | 3/2011 | Lamprecht et al. |
| 2011/0118707 A1 | 5/2011 | Burbank |
| 2011/0118748 A1 | 5/2011 | Itkowitz |
| 2011/0118753 A1 | 5/2011 | Itkowitz et al. |
| 2011/0137337 A1 | 6/2011 | van den Dool et al. |
| 2011/0190932 A1 | 8/2011 | Tsusaka et al. |
| 2011/0230894 A1 | 9/2011 | Simaan et al. |
| 2011/0238079 A1 | 9/2011 | Hannaford et al. |
| 2011/0276058 A1 | 11/2011 | Choi et al. |
| 2011/0279374 A1 | 11/2011 | Park et al. |
| 2011/0282493 A1 | 11/2011 | Ortmaier |
| 2011/0288579 A1 | 11/2011 | Hyodo |
| 2011/0306952 A1 | 12/2011 | Chen et al. |
| 2012/0071752 A1 | 3/2012 | Sewell et al. |
| 2012/0165828 A1 | 6/2012 | Duque et al. |
| 2012/0191245 A1 | 7/2012 | Fudaba et al. |

FOREIGN PATENT DOCUMENTS

| | | |
|---|---|---|
| EP | 2 298 220 A1 | 3/2011 |
| EP | 2 332 484 A2 | 6/2011 |
| JP | 63-029810 A | 2/1988 |
| JP | 64-034688 A | 2/1989 |
| JP | 01-271185 A | 10/1989 |
| JP | 02-071980 A | 3/1990 |
| JP | 02-292193 A | 12/1990 |
| JP | 03-161289 A | 7/1991 |
| JP | 05-096477 A | 4/1993 |
| JP | 5-329784 A | 12/1993 |
| JP | 07-001366 A | 1/1995 |
| JP | 07-194609 A | 8/1995 |
| JP | 07-241300 A | 9/1995 |
| JP | 07-246578 A | 9/1995 |
| JP | 07-096182 B2 | 10/1995 |
| JP | 8-66883 A | 3/1996 |
| JP | 08-215204 A | 8/1996 |
| JP | 08-243080 A | 9/1996 |
| JP | H10-502265 A | 3/1998 |
| JP | 10-128538 A | 5/1998 |
| JP | 11-300662 A | 11/1999 |
| JP | 2000-312684 A | 11/2000 |
| JP | 2001-087281 A | 4/2001 |
| JP | 2001-113481 A | 4/2001 |
| JP | 2001-277157 A | 10/2001 |
| JP | 2001-309920 A | 11/2001 |
| JP | 2002-014287 A | 1/2002 |
| JP | 2002-059380 A | 2/2002 |
| JP | 2002-102248 A | 4/2002 |
| JP | 2002-272758 A | 9/2002 |
| JP | 2002-537884 A | 11/2002 |
| JP | 2003-024336 A | 1/2003 |
| JP | 2003-053685 A | 2/2003 |
| JP | 2003-250812 A | 9/2003 |
| JP | 2003-265500 A | 9/2003 |
| JP | 2003-340752 A | 12/2003 |
| JP | 2004-105451 A | 4/2004 |
| JP | 2004-114201 A | 4/2004 |
| JP | 2005-511185 A | 4/2005 |
| JP | 2005-192743 A | 7/2005 |
| JP | 3686947 B2 | 8/2005 |
| JP | 2005-261827 A | 9/2005 |
| JP | 2005-283600 A | 10/2005 |

(56) References Cited

FOREIGN PATENT DOCUMENTS

| | | |
|---|---|---|
| JP | 2005-312991 A | 11/2005 |
| JP | 2006-061272 A | 3/2006 |
| JP | 2006-167867 A | 6/2006 |
| JP | 2006-288955 A | 10/2006 |
| JP | 2006-321027 A | 11/2006 |
| JP | 2007-029274 A | 2/2007 |
| JP | 2007-038315 A | 2/2007 |
| JP | 2007-98507 A | 4/2007 |
| JP | 2007-105485 A | 4/2007 |
| JP | 3999816 B2 | 10/2007 |
| JP | 2008-000282 A | 1/2008 |
| JP | 2008-036793 A | 2/2008 |
| JP | 4058113 B2 | 3/2008 |
| JP | 2008-093270 A | 4/2008 |
| JP | 2008-104854 A | 5/2008 |
| JP | 2008-514357 A | 5/2008 |
| JP | 2008-173724 A | 7/2008 |
| JP | 2008-188109 A | 8/2008 |
| JP | 4129313 B2 | 8/2008 |
| JP | 4176126 B2 | 11/2008 |
| JP | 2009-028157 A | 2/2009 |
| JP | 2009-056164 A | 3/2009 |
| JP | 2009-512514 A | 3/2009 |
| JP | 2009-520573 A | 5/2009 |
| JP | 2009-178230 A | 8/2009 |
| JP | 2009-178541 A | 8/2009 |
| JP | 2009-530037 A | 8/2009 |
| JP | 2009-195694 A | 9/2009 |
| JP | 2009-226029 A | 10/2009 |
| JP | 2009-226093 A | 10/2009 |
| JP | 2009-269127 A | 11/2009 |
| JP | 2010-504127 A | 2/2010 |
| JP | 2010-076012 A | 4/2010 |
| JP | 2010-524548 A | 7/2010 |
| JP | 2011-509112 A | 3/2011 |
| JP | 2011-206213 A | 10/2011 |
| JP | 2012-000199 A | 1/2012 |
| JP | 2012-091310 A | 5/2012 |
| WO | 96/00044 A1 | 1/1996 |
| WO | 97/16123 A1 | 5/1997 |
| WO | 97/16124 A1 | 5/1997 |
| WO | 97/29690 A1 | 8/1997 |
| WO | 98/25666 A1 | 6/1998 |
| WO | 00/51486 A1 | 9/2000 |
| WO | 00/60421 A2 | 10/2000 |
| WO | 03/049596 A2 | 6/2003 |
| WO | 2006/039092 A2 | 4/2006 |
| WO | 2006/111966 A2 | 10/2006 |
| WO | 2007/047782 A2 | 4/2007 |
| WO | 2007/075864 A1 | 7/2007 |
| WO | 2007/111955 A2 | 10/2007 |
| WO | 2007/126443 A2 | 11/2007 |
| WO | 2007/138674 A1 | 12/2007 |
| WO | 2008/038184 A2 | 4/2008 |
| WO | 2008/108289 A1 | 9/2008 |
| WO | 2009/034477 A2 | 3/2009 |
| WO | 2009/089614 A1 | 7/2009 |
| WO | 2010/006057 A1 | 1/2010 |
| WO | 2010/093152 A2 | 8/2010 |
| WO | 2010/109932 A1 | 9/2010 |
| WO | 2010/126127 A1 | 11/2010 |
| WO | 2011/025786 A1 | 3/2011 |
| WO | 2011/060139 A2 | 5/2011 |
| WO | 2011/060185 A1 | 5/2011 |
| WO | 2011/060187 A1 | 5/2011 |
| WO | 2011/085815 A1 | 7/2011 |
| WO | 2012/042949 A1 | 4/2012 |

OTHER PUBLICATIONS

U.S. Office Action dated May 8, 2015 received in related U.S. Appl. No. 14/157,920.
Chinese Office Action dated Jun. 3, 2015 from related Chinese Application No. 2012800359263, together with an English language translation.
Chinese Office Action dated Jul. 1, 2015 from related Chinese Application No. 2012800372446, together with an English language translation.
Extended Supplementary European Search Report dated Jul. 1, 2015 from related European Application No. 12 82 0066.4.
Extended Supplementary European Search Report dated Jul. 2, 2015 from related European Application No. 12 81 9672.2.
Extended Supplementary European Search Report dated Jul. 23, 2015 from related European Application No. 12 81 9455.2.
Notice of Allowance dated Jan. 20, 2015 from related U.S. Appl. No. 13/566,023.
Notice of Allowance dated Jan. 29, 2015 from related U.S. Appl. No. 14/168,551.
Extended Supplementary European Search Report dated Feb. 12, 2015 from related European Application No. 12 81 9447.9.
Extended Supplementary European Search Report dated Feb. 13, 2015 from related European Application No. 12 82 0679.4.
Supplementary European Search Report dated Feb. 18, 2015 from related European Application No. 12 82 0758.6.
Extended Supplementary European Search Report dated Feb. 23, 2015 from related European Application No. 12 81 9877.7.
Extended Supplementary European Search Report dated Feb. 23, 2015 from related European Application No. 12 82 0239.7.
Partial Supplementary European Search Report dated Feb. 26, 2015 from related European Application No. 12 82 0066.4.
Partial Supplementary European Search Report dated Feb. 27, 2015 from related European Application No. 12 81 9672.2.
Extended Supplementary European Search Report dated Mar. 2, 2015 from related European Application No. 12 82 0017.7.
Extended Supplementary European Search Report dated Mar. 16, 2015 from related European Application No. 12 82 0479.9.
Extended Supplementary European Search Report dated Mar. 16, 2015 from related European Application No. 12 81 9504.7.
Extended Supplementary European Search Report dated Mar. 16, 2015 from related European Application No. 12 81 9398.4.
Office Action dated Mar. 25, 2015 received in related U.S. Appl. No. 14/169,321.
Extended Supplementary European Search Report dated Mar. 27, 2015 from related European Application No. 12 82 0056.5.
English Abstract of JP 01-234140 dated Sep. 19, 1989.
International Search Report dated Oct. 23, 2012 issued in PCT/JP2012/070414.
International Search Report dated Sep. 4, 2012 issued in PCT/JP2012/070408.
International Search Report dated Aug. 28, 2012 issued in PCT/JP2012/069927.
International Search Report dated Sep. 4, 2012 issued in PCT/JP2012/070415.
International Search Report dated Oct. 16, 2012 issued in PCT/JP2012/070581.
International Search Report dated Nov. 13, 2012 issued in PCT/JP2012/070576.
International Search Report dated Sep. 18, 2012 issued in PCT/JP2012/070417.
International Search Report dated Oct. 30, 2012 issued in PCT/JP2012/070418.
International Search Report dated Sep. 11, 2012 issued in PCT/JP2012/070416.
International Search Report dated Sep. 18, 2012 issued in PCT/JP2012/070407.
International Search Report dated Sep. 18, 2012 issued in PCT/JP2012/069868.
International Search Report dated Nov. 6, 2012 issued in PCT/JP2012/069919.
International Search Report dated Sep. 11, 2012 issued in PCT/JP2012/069696.
Office Action dated Oct. 22, 2015 received in related U.S. Appl. No. 14/151,987.
Office Action dated Nov. 19, 2015 received in related U.S. Appl. No. 14/157,920.

(56) References Cited

OTHER PUBLICATIONS

Office Action dated Sep. 16, 2015 received in related U.S. Appl. No. 13/566,012.
Office Action dated Feb. 22, 2016 received in related U.S. Appl. No. 14/168,496.
Office Action dated Mar. 10, 2016 received in related U.S. Appl. No. 13/566,012.
Japanese Office Action dated Jan. 19, 2016 from related Japanese Patent Application No. 2012-036226, together with an English language translation.
Office Action dated Mar. 24, 2016 received in related U.S. Appl. No. 13/566,047.
Japanese Office Action dated Apr. 26, 2016 from related Japanese Patent Application No. 2012-157788.
Japanese Office Action dated Apr. 26, 2016 from related Japanese Patent Application No. 2012-154945.
Notice of Allowance dated Apr. 22, 2016 issued in U.S. Appl. No. 14/157,920.
Japanese Office Action dated Feb. 26, 2016 from related Japanese Patent Application No. 2012-157788.
Japanese Office Action dated Feb. 26, 2016 from related Japanese Patent Application No. 2012-154945.
Japanese Office Action dated Jun. 14, 2016 in related Japanese Patent Application No. 2012-012104.
Office Action dated Jun. 16, 2016 received in related U.S. Appl. No. 14/169,742.
Japanese Office Action dated Jun. 28, 2016 in related Japanese Patent Application No. 2013-526973.
European Patent Office Communication dated May 23, 2016 in related European Application No. 12 819 877.7.
Office Action dated May 9, 2016 received in related U.S. Appl. No. 14/170,856.
Notice of Allowance dated Jan. 4, 2017 in related Japanese Patent Application No. 2012-012104.

* cited by examiner

MEDICAL MANIPULATOR

This application is a continuation application based on a PCT International Application No. PCT/JP2012/070416, filed on Aug. 3, 2012, whose priority is claimed on U.S. Provisional application No. 61/515,203 filed on Aug. 4, 2011 and Japanese Patent Application No. 2012-157788 filed on Jul. 13, 2012. The contents of all of the PCT Application, the U.S. Provisional Application and the Japanese Patent Application are incorporated by reference herein.

BACKGROUND OF THE INVENTION

1. Field of the Invention

The present invention relates to a medical manipulator.

2. Description of Related Art

In order to assist a procedure of an operator, a medical manipulator (hereinafter, simply referred to as "a manipulator") configured to detachably hold a treatment tool and move the treatment tool to perform treatment is being considered.

As such a manipulator, for example, a manipulator disclosed in U.S. Pat. No. 6,645,196 is well known.

In the manipulator, a sensor for detecting a motion of the manipulator is installed. Furthermore, various treatment tools are detachably installed with respect to the manipulator. A control device is installed in the manipulator. The control device has a processing device and a recording unit. A motion of the manipulator is controlled by the control device.

A user interface and a master manipulator are connected to the control device. The user interface has a CRT monitor, a keyboard, or the like.

A sensor for a master installed at the master manipulator detects the motion of the master manipulator. The motion of the master manipulator manipulated by the operator is detected by the sensor for a master, and the manipulator and the treatment tool are operated based on the motion.

Here, after treatment is performed by the treatment tool in the treatment region in the body cavity of a patient, the treatment tool is extracted from the treatment section. Before the treatment tool is removed from the manipulator, a dimension or disposition of the treatment tool before and after exchange is electrically stored in the recording unit. A distal end of the treatment tool after exchange can be automatically disposed on the treatment region of the patient by the manipulator can being moved based on the electrically stored information.

SUMMARY OF THE INVENTION

According to a first aspect of the present invention, a medical manipulator includes a base section at which a support surface is formed; a movable part movably supported on the support surface, between a distal end position, which is a distal end side in the reference direction, and a proximal end position, which is a proximal end side in the reference direction, with respect to the base section, when the reference direction parallel to the support surface is defined; a positioning mechanism configured to position the movable part at the distal end position with respect to the base section; a holding section movably supported in the reference direction with respect to the movable part, and configured to detachably hold a proximal end portion of a treatment tool such that a longitudinal direction of the treatment tool having an elongated shape is substantially parallel to the reference direction; and a driving unit configured to move the holding section in the reference direction with respect to the movable part.

According to a second aspect of the present invention, in the medical manipulator according to the first aspect of the present invention, the positioning mechanism includes an engaging section provided at one of the base section and the movable part, and an engaged device having an engaged section provided at other of the base section and the movable part and restricted movement to the reference direction on engaging with the engaging section, wherein the engaged device includes a support member configured to support the engaged section and a biasing member configured to bias the support member such that the engaged section engages with the engaging section.

According to a third aspect of the present invention, in the medical manipulator according to the second aspect of the present invention, the engaged device includes a rotating shaft configured to rotatably connect the other of the base section and the movable part to the support member, and the biasing member biases the support member to rotate about the rotating shaft.

According to a fourth aspect of the present invention, in the medical manipulator according to the third aspect of the present invention, wherein the support member has a rod shape, the support member is supported by the rotating shaft at an intermediate section in an extension direction in which the support member extends, the engaged section is provided at a first end portion of the support member, which is a distal end side in the reference direction, and a second end portion of the support member is disposed at the proximal end side in the reference direction with respect to the first end portion of the support member.

According to a fifth aspect of the present invention, in the medical manipulator according to the fourth aspect of the present invention, the positioning mechanism includes a pair of engaging sections and a pair of engaged devices, the pair of engaging sections are provided so as to separate from each other in a perpendicular direction perpendicular to the reference direction parallel to the support surface, the engaged sections of the engaged devices are configured to be disposed between the pair of engaging sections, and the biasing member biases the first end portions of the support members to make the first end portions of the support members being separated from each other.

According to a sixth aspect of the present invention, in the medical manipulator according to any one aspect of the first to fifth aspects of the present invention, the positioning mechanism positions the movable part at the proximal end position with respect to the base section.

According to a seventh aspect of the present invention, in the medical manipulator according to any one aspect of the first to sixth aspects of the present invention, the medical manipulator includes a position detecting unit configured to detect a distal end disposition state in which the movable part is disposed at the distal end position with respect to the base section or a non-distal end disposition state in which the movable part is not disposed at the distal end position with respect to the base section; an input unit configured to output a manipulation signal to control the driving unit based on an input from an operator; a control unit having a driving mode of controlling movement in the reference direction of the holding section by the driving unit and a standby mode of not controlling the driving unit based on the manipulation signal, and configured to select the driving mode when the position detecting unit detects the distal end disposition state and the standby mode when the position detecting unit detects the non-distal end disposition state.

According to an eighth aspect of the present invention, in the medical manipulator according to any one aspect of the first to seventh aspects of the present invention, the medical manipulator includes a biasing mechanism configured to bias the movable part to the proximal end side in the reference direction with respect to the base section.

According to a ninth aspect of the present invention, in the medical manipulator according to the eighth aspect of the present invention, a biasing force applied to bias the movable part by the biasing mechanism is constant regardless of a position in the reference direction of the movable part with respect to the base section.

According to a tenth aspect of the present invention, in the medical manipulator according to any one aspect of the first to seventh aspects of the present invention, when the movable part is moved to the proximal end side in the reference direction with respect to the base section, the movable part can be removed from the base section.

According to an eleventh aspect of the present invention, in the medical manipulator according to any one aspect of the first to tenth aspects of the present invention, a length in a longitudinal direction of the treatment tool is set to be smaller than a length in the reference direction between the distal end position and the proximal end position.

According to a twelfth aspect of the present invention, in the medical manipulator according to any one aspect of the first to eleventh aspects of the present invention, lengths in the longitudinal direction of a plurality of treatment tools detachably held by the holding section are equal to each other.

DETAILED DESCRIPTION OF THE INVENTION

First Embodiment

Hereinafter, an operation support apparatus using a medical manipulator according to the first embodiment of the present invention will be described with reference to FIGS. 1 to 12.

Figure 1:
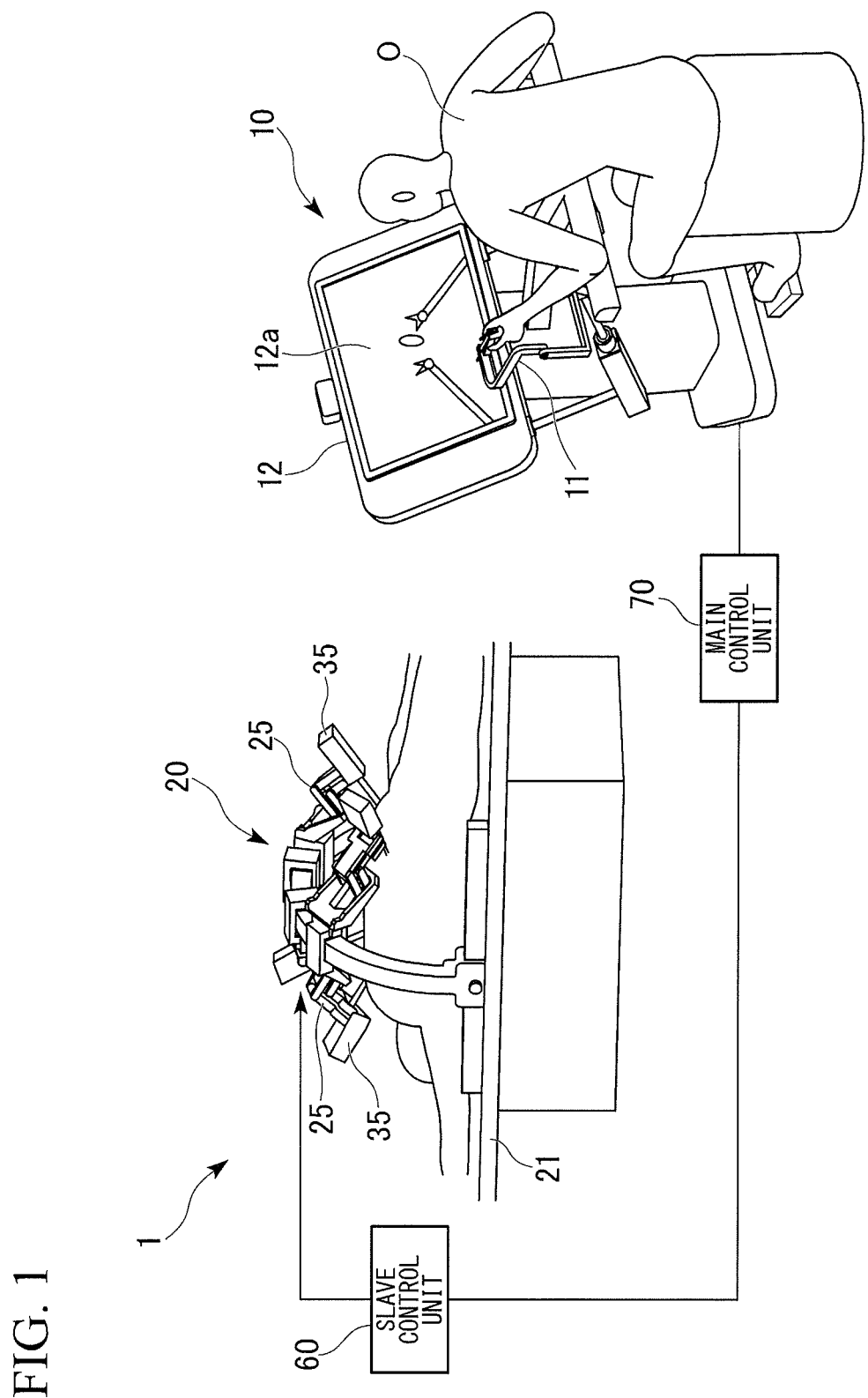
FIG. 1 is an overall view showing an operation support apparatus using a medical manipulator according to a first embodiment of the present invention.

As shown in FIG. 1, an operation support apparatus 1 includes a master manipulation input unit 10, a slave manipulator (a medical manipulator) 20 of the present invention, and a main control unit 70 connected to the master manipulation input unit 10 and the slave manipulator 20.

The master manipulation input unit 10 functions as a master of the operation support apparatus 1. The master manipulation input unit 10 has a manipulation unit (an input unit) 11 and a display unit 12.

The manipulation unit 11 is fixed to, for example, the display unit 12. The manipulation unit 11 outputs a manipulation signal for controlling the slave manipulator 20 based on manipulation (input) from an operator O such as a surgeon or the like.

The display unit 12 has a display panel 12a such as a liquid crystal panel or the like. An image signal obtained by an observing apparatus such as an endoscope apparatus or the like is processed by the main control unit 70 to be displayed on the display unit 12.

Figure 2:
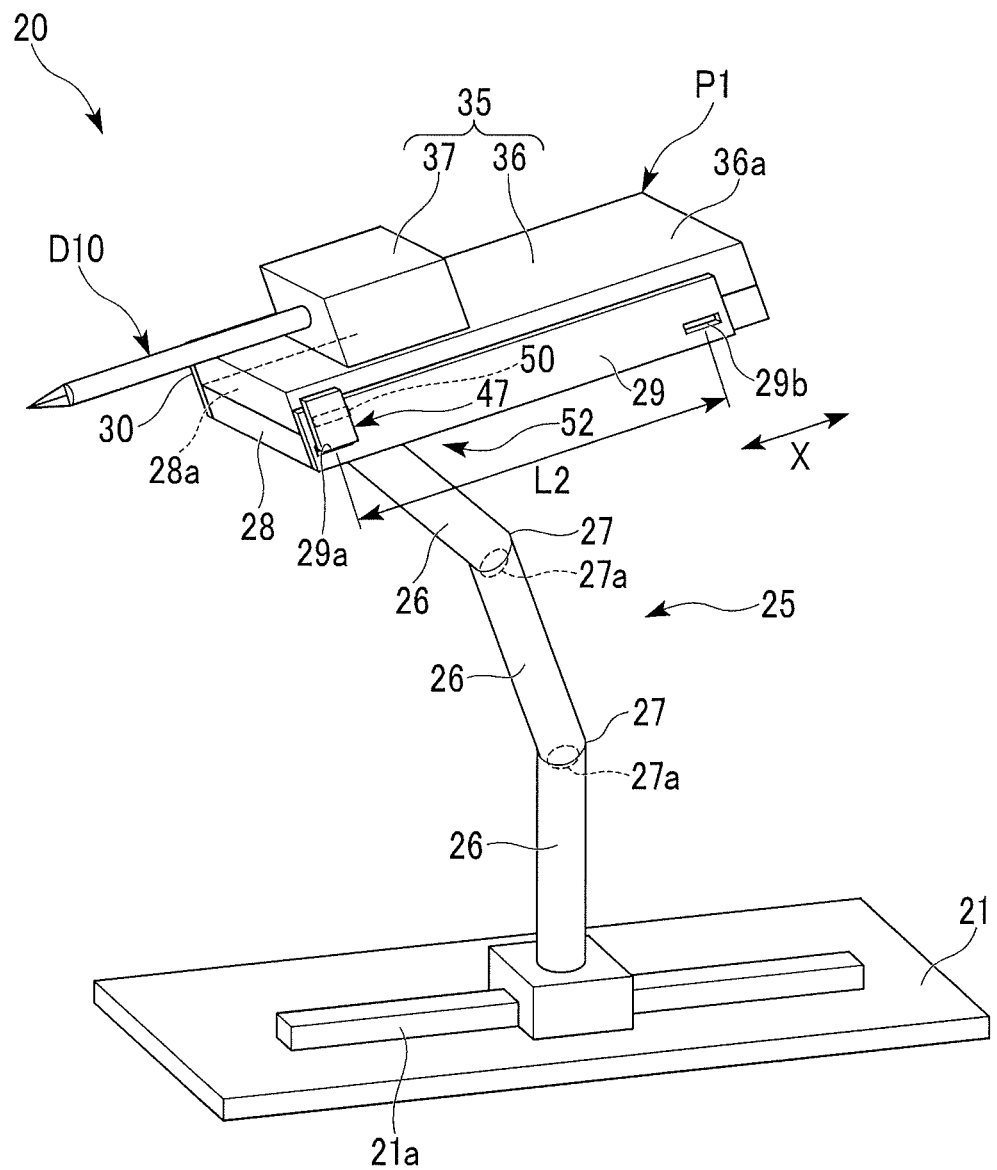
FIG. 2 is a perspective view showing the medical manipulator according to the first embodiment of the present invention when a slide table is fixed to a distal end position.

As shown in FIGS. 1 and 2, the slave manipulator 20 has a slave arm (a base section) 25 attached on a base 21, a movable holding section 35 movably supported in a reference direction X with respect to the slave arm 25, and a slave control unit (a control unit) 60 configured to control the slave arm 25 and the movable holding section 35. In addition, the slave manipulator 20 includes a plurality of sets of slave arms 25 and movable holding sections 35. In FIG. 2, for the convenience of description, only one set of the slave arm 25 and the movable holding section 35 are shown.

As shown in FIG. 2, the slave arm 25 is configured such that end portions of a plurality of rods 26 are rotatably connected to each other via joint sections 27. An actuator 27a is installed at the joint section 27. As the actuator 27a is provided, an angle formed between the adjacent rods 26 can be adjusted.

A lower end portion of the slave arm 25 is slidably attached to a rail 21a installed at the base 21. Meanwhile, a bottom surface of a box-shaped base plate 28 is connected (coupled) to a distal end of the slave arm 25, that is, an end portion of the rod 26. In the base plate 28, a top surface (a support surface) 28a opposite to a bottom surface has a rectangular shape and is a substantially flat surface. Here, a direction parallel to long sides of the top surface 28a is defined as the reference direction X. Side plates 29 and 30 extending upward from side surfaces beyond the top surface 28a are fixed to the side surfaces parallel to the reference direction X in the base plate 28.

A through-hole (an engaging section) 29a penetrating the side plate 29 is formed at a distal end side in the reference direction X of the side plate 29. Similarly, a through-hole (an engaging section) 29b having the same shape as the through-hole 29a is formed toward the base end side from the through-hole 29a in the side plate 29.

Figure 3:
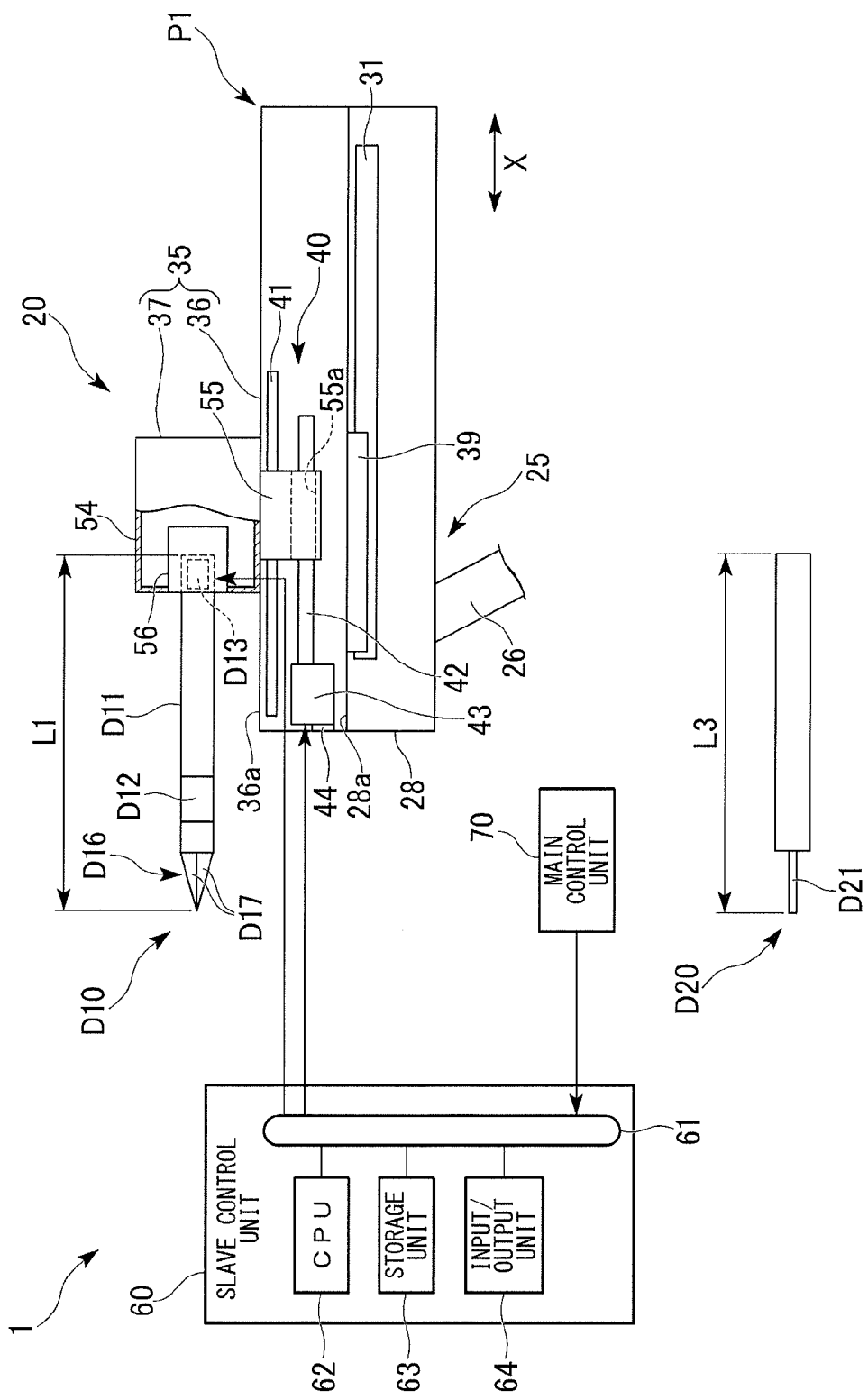
FIG. 3 is a view schematically showing a configuration of main parts of the medical manipulator according to the first embodiment of the present invention.

As shown in FIG. 3, a pair of base slide rails 31 are attached to inside of the base plate 28 (one of the base slide rails 31 is not shown). The base slide rails 31 are disposed parallel to each other in the base plate 28 to extend in the reference direction X.

As shown in FIGS. 2 and 3, the movable holding section 35 has a box-shaped slide table (a movable part) 36, and a holding unit (a holding section) 37 supported on a top surface 36a of the slide table 36. A pair of base slide guides 39 are fixed to a bottom surface of the slide table 36 (one of the base slide guides 39 is not shown). The base slide guides 39 are slidably fitted to the base slide rails 31 in the reference direction X. Specifically, for example, the base slide guides 39 having a substantially tubular shape are fitted to surround an outer circumferential surface of the base slide rail 31 having substantially a rod shape. The slide table 36 supported on the top surface 28a of the base plate 28 is disposed to be sandwiched between the side plates 29 and 30.

As described above, an assistant or the like can manually move the slide table 36 in the reference direction X with respect to the base plate 28.

Further, when the slide table 36 is moved in the reference direction X with respect to the base plate 28 to the proximal end side, the slide table 36 can be removed from the base plate 28. In addition, the slide table 36, which is removed, fits the base slide guides 39 to the base slide rail 31 and moves the slide table 36 in the reference direction X with respect to the base plate 28 to the distal end side, enabling attachment to the base plate 28.

A holding unit driving device (a driving unit) 40 is installed in the slide table 36. Specifically, the holding unit driving device 40 has a pair of table slide rails 41 (one of the table slide rails 41 is not shown) attached to the slide table 36, a ball screw 42 disposed parallel to the reference direction X, and a servo motor 43 configured to rotate the ball screw 42 about an axis thereof.

The table slide rails 41 are disposed to extend in the reference direction X. The servo motor 43 is attached to the slide table 36 via a motor support section 44.

Figure 4:
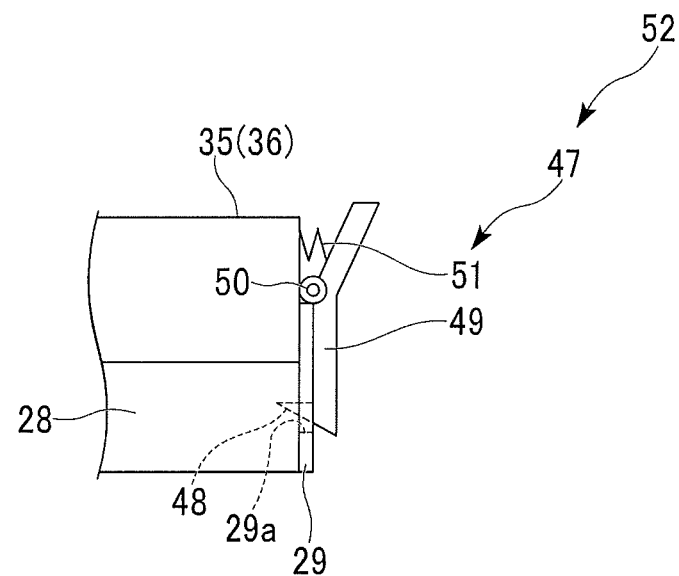
FIG. 4 is a front view showing main parts of a slave arm and a movable holding section of the medical manipulator according to the first embodiment of the present invention.

As shown in FIGS. 2 and 4, a rotating claw unit (an engaged device) 47 is attached to a side surface of the slide table 36.

The rotating claw unit 47 includes a support member 49 in which claws (an engaged section) 48 engaged with the through-holes 29a and 29b are formed at one end portion thereof, a rotating shaft 50 rotatably connecting the slide table 36 and a center portion of the support member 49, and a spring member (a biasing member) 51 configured to bias the support member 49 such that the claws 48 are engaged with the through-holes 29a and 29b.

The rotating shaft 50 is disposed at a side surface of the slide table 36 such that a rotating axis thereof is disposed to be parallel to the reference direction X. One end portion of the support member 49 is disposed to sandwich the side plate 29 between the slide table 36 and the support member 49. The claw 48 is formed at a surface of one end portion of the support member 49 in the side plate 29 side. The spring member 51 is connected to the slide table 36 and the other end portion of the support member 49.

As described above, the slide table 36 can be moved in the reference direction X with respect to the base plate 28. Then, when the slide table 36 is disposed at a distal end position P1 (see FIG. 2), which is a position of the most distal end side within a movable range of the slide table 36 in the reference direction X, the claw 48 is engaged with the through-hole 29a.

In a natural state in which an assistant does not apply a force to the support member 49, as the spring member 51 biases the other end portion of the support member 49 to be separated from the slide table 36, the support member 49 is rotated about the rotating shaft 50 to move one end portion of the support member 49 toward the side plate 29. Since the claw 48 cannot be moved in the reference direction X with respect to the through-hole 29a when the claw 48 is engaged with the through-hole 29a, movement of the slide table 36 in the reference direction X with respect to the base plate 28 is restricted.

A positioning mechanism 52 of the present embodiment is configured by the through-holes 29a and 29b, and the rotating claw unit 47.

As described above, in the present first embodiment, the slide table 36 can be positioned (fixed) at the distal end position P1 with respect to the base plate 28.

Figure 5:
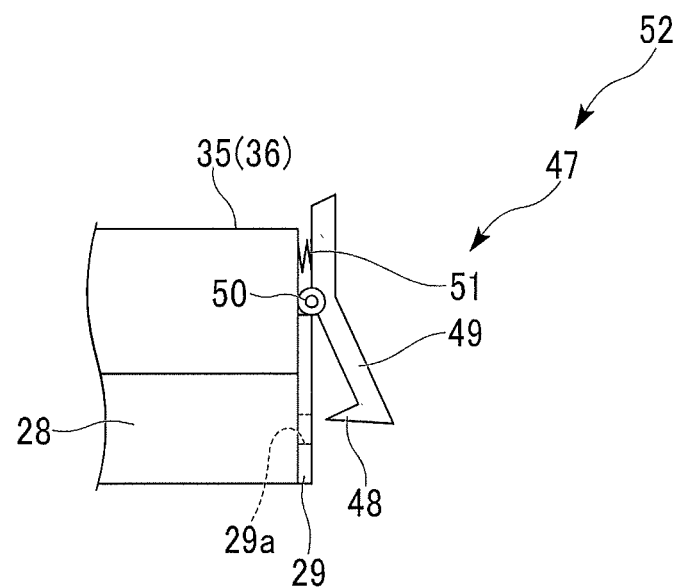
FIG. 5 is a front view of the slave arm and the movable holding section according to the first embodiment of the present invention when a support member is rotated.

In addition, as shown in FIG. 5, as the assistant presses the other end portion of the support member 49 toward the slide table 36 against a biasing force of the spring member 51, the support member 49 can be rotated about the rotating shaft 50 to release engagement of the through-hole 29a with the claw 48.

Figure 6:
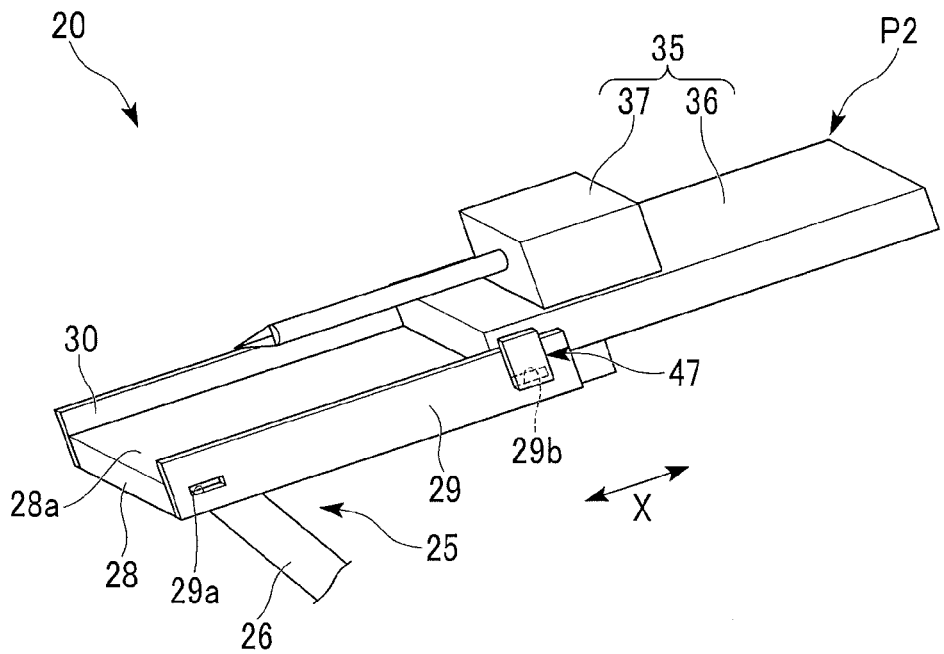
FIG. 6 is a perspective view of main parts of the medical manipulator according to the first embodiment of the present invention when the slide table is fixed to a proximal end position.

Further, as shown in FIG. 6, as the slide table 36 is moved toward the proximal end side in the reference direction X with respect to the base plate 28, a position of the slide table 36 with respect to the base plate 28 becomes a proximal end position P2 when the claw 48 of the rotating claw unit 47 is engaged with the through-hole 29b. That is, even at the proximal end position P2, the slide table 36 can be positioned with respect to the base plate 28.

As shown in FIG. 3, in the holding unit 37, a table slide guide 55 is fixed to a bottom surface of a unit main body 54 having a box shape. The table slide guide 55 is slidably fitted to the table slide rails 41 in the reference direction X. Further, a female-threaded section 55a formed at the table slide guide 55 is screwed with the ball screw 42.

The servo motor 43 turns the ball screw 42 about an axis thereof in a desired direction. As the ball screw 42 is turned by the servo motor 43, the table slide guide 55 is moved in the reference direction X by the ball screw 42 being screwed with the female-threaded section 55*a*. For this reason, the holding unit 37 can be moved on the top surface 36*a* of the slide table 36 in the reference direction X with respect to the slide table 36.

A well-known holding mechanism 56 is attached to the unit main body 54 while being exposed from the distal end side in the reference direction X. In addition, the holding mechanism 56 may be attached from the proximal end side in the reference direction X. Further, the holding mechanism 56 may be attached from above regardless of the reference direction X. An attachment direction of the holding mechanism 56 is not specifically limited.

A proximal end portion of the treatment tool having an elongated shape such as a forceps D10 or the like is detachably mounted on the holding mechanism 56. The treatment tool mounted on the holding mechanism 56 is not limited to the forceps D10, and a high frequency incision tool, a local injection needle, or the like may be appropriately selected. In the following example, a case in which the forceps D10 and a high frequency incision tool D20 are used as the treatment tool will be described.

In the forceps D10, a treatment section D16 having a pair of forceps pieces D17 is installed at a distal end portion of a treatment tool inserting section D11 having a substantially cylindrical column shape. A curved section D12 that can be bent is installed at the distal end side of the treatment tool inserting section D11.

A driving unit D13 having a motor is installed in the proximal end side of the treatment tool inserting section D11. A distal end portion of a manipulation wire (not shown) is connected to the forceps piece D17 or the curved section D12. As the manipulation wire is manipulated to advance or retreat by the driving unit D13, the pair of forceps pieces D17 can be opened and closed, and the curved section D12 can be bent in a desired direction.

A length L1 in a longitudinal direction of the forceps D10 having the above-mentioned configuration is set to be smaller than a length in the reference direction X between the distal end position P1 and the proximal end position P2 of the slide table 36, in other words, a pitch L2 in the reference direction X of the through-holes 29*a* and 29*b* shown in FIG. 2.

Figure 9:
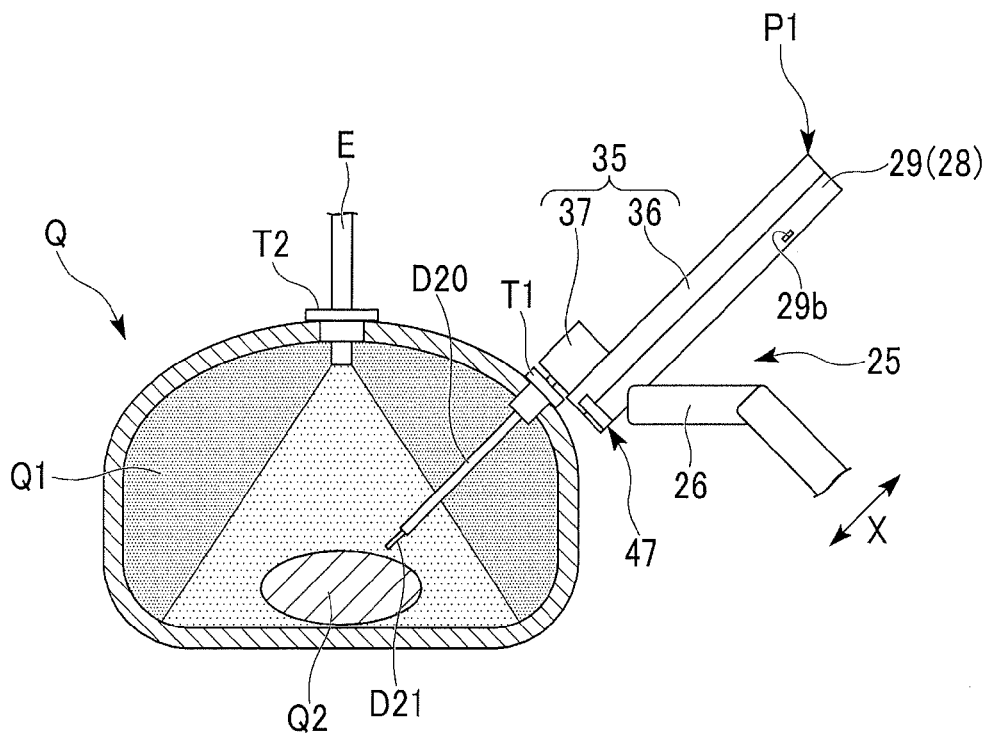
FIG. 9 is a schematic view for describing the procedure using the operation support apparatus according to the first embodiment of the present invention.

Further, as shown in FIG. 3, the high frequency incision tool D20, which is another treatment tool having an elongated shape different from that of the forceps D10, is detachably mounted on the holding mechanism 56 (see FIG. 9). A length L3 in the longitudinal direction of the high frequency incision tool D20 is set to be equal to the length L1 of the forceps D10.

The holding mechanism 56 holds the proximal end portion of the forceps D10 such that the longitudinal direction of the forceps D10 is substantially parallel to the reference direction X. The holding mechanism 56 also holds the high frequency incision tool D20 in the same manner. In addition, while not shown, when the holding mechanism 56 holds the high frequency incision tool D20, a high frequency voltage can be applied to a cutting part D21 of the high frequency incision tool D20 from a high frequency power supply via the holding mechanism 56.

When the operation support apparatus 1 is used, an endoscope apparatus (not shown) is attached to the movable holding section 35 of the other slave arm 25, and an image acquired by the endoscope apparatus is displayed on the display panel 12*a* to perform procedure.

A slave control unit 60 has a CPU 62 connected to a bus 61, a storage unit 63 and an input/output unit 64. The servo motor 43, the main control unit 70 and the actuator 27*a* (not shown) of the slave manipulator 20 are connected to the bus 61. The bus 61 is configured such that the driving unit D13 of the forceps D10 can be connected when the forceps D10 is held by the holding mechanism 56.

A program for driving the actuator 27*a* or the servo motor 43 to move the slave manipulator 20 is stored in the storage unit 63.

The CPU 62 reads the program from the storage unit 63 when the operation support apparatus 1 is started. Then, the slave manipulator 20 is operated based on the program and a manipulation signal output from the manipulation unit 11, or the like.

The input/output unit 64 is, for example, a keyboard or a display panel. The assistant inputs an instruction from the keyboard while checking a manipulation state on the display panel 12*a*. The input instruction is transmitted to the CPU 62.

The main control unit 70 includes a power supply (not shown) to supply power to the master manipulation input unit 10 and the slave manipulator 20.

The manipulation signal output from the manipulation unit 11 of the master manipulation input unit 10 is transmitted to the slave control unit 60. The slave control unit 60 processes a signal of the image acquired by the endoscope apparatus attached to the movable holding section 35 of the slave arm 25, and outputs the signal, which is processed, to the display unit 12.

Next, the procedure using the operation support apparatus 1 having the above-mentioned configuration will be described focusing on the motion of the slave manipulator 20. Hereinafter, an example of a case in which the treatment tool is introduced into the body cavity of the patient to treat the target tissue will be described.

In addition, conventionally, the slide table 36 is disposed at the distal end position P1 with respect to the base plate 28. Then, as the claw 48 is engaged with the through-hole 29*a*, the slide table 36 is fixed to the base plate 28.

When the operation support apparatus 1 is started, power is supplied to the master manipulation input unit 10 and the slave manipulator 20 from the power supply of the main control unit 70. In the slave manipulator 20, the CPU 62 reads the program from the storage unit 63.

Figure 7:
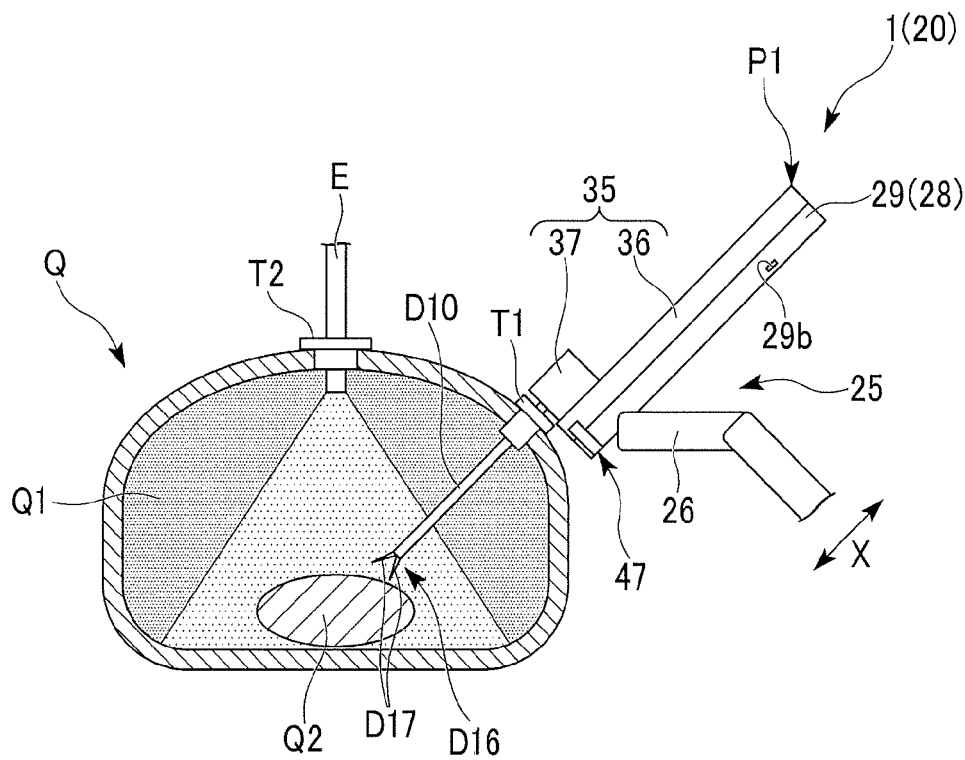
FIG. 7 is a schematic view for describing a procedure using the operation support apparatus according to the first embodiment of the present invention.

As the assistant manipulates the input/output unit 64 to drive the servo motor 43, the holding unit 37 is moved to the proximal end side in the reference direction X with respect to the slide table 36. The forceps D10 is attached to the holding mechanism 56 of the holding unit 37. The slave arm 25 is operated, and as shown in FIG. 7, the forceps D10 is disposed on the same axis as a trocar T1 attached to a patient Q.

An endoscope apparatus E is introduced into a body cavity Q1 of the patient Q from a trocar T2 different from the trocar T1, and the image acquired by the endoscope apparatus E is output on the display unit 12.

The assistant drives the servo motor 43 to move the holding unit 37 to the distal end side in the reference direction X with respect to the slide table 36 to introduce the forceps D10 into the body cavity Q1 through the trocar T1, while checking the image displayed on the display unit 12. The forceps D10 is held to be substantially parallel to the reference direction X in which the holding unit 37 is moved. For this reason, the forceps D10 can be easily introduced into the trocar T1.

In addition, the forceps D10 upon introduction into the body cavity Q1 is configured in a state in which the pair of forceps pieces D17 are separated from each other to be opened and the curved section D12 is straightened, not being curved.

A driving amount of the servo motor 43 is adjusted to cause the treatment section D16 of the introduced forceps D10 to approach a target tissue Q2 in the body cavity Q1.

As the operator O manipulates the manipulation unit 11 to drive the driving unit D13, the pair of forceps pieces D17 are manipulated to be opened and closed while appropriately bending the curved section D12. As a result, treatment with respect to the target tissue Q2 is performed.

As described above, a motion of finally introducing the forceps D10 into the body cavity Q1 and a motion of adjusting a position of the forceps D10 in the body cavity Q1 are performed by fixing the slave arm 25 and driving the servo motor 43.

Next, a sequence of completing treatment by the forceps D10 and exchanging the treatment tool attached to the holding unit 37 with the high frequency incision tool D20 from the forceps D10 will be described.

Previously, the manipulation unit 11 is manipulated so that the forceps D10 is in an open state and the curved section D12 is set to a straight state.

First, in a state in which a position of the holding unit 37 with respect to the slide table 36 is fixed, one end portion of the support member 49 is manipulated to release engagement of the through-hole 29a with the claw 48.

Figure 8:
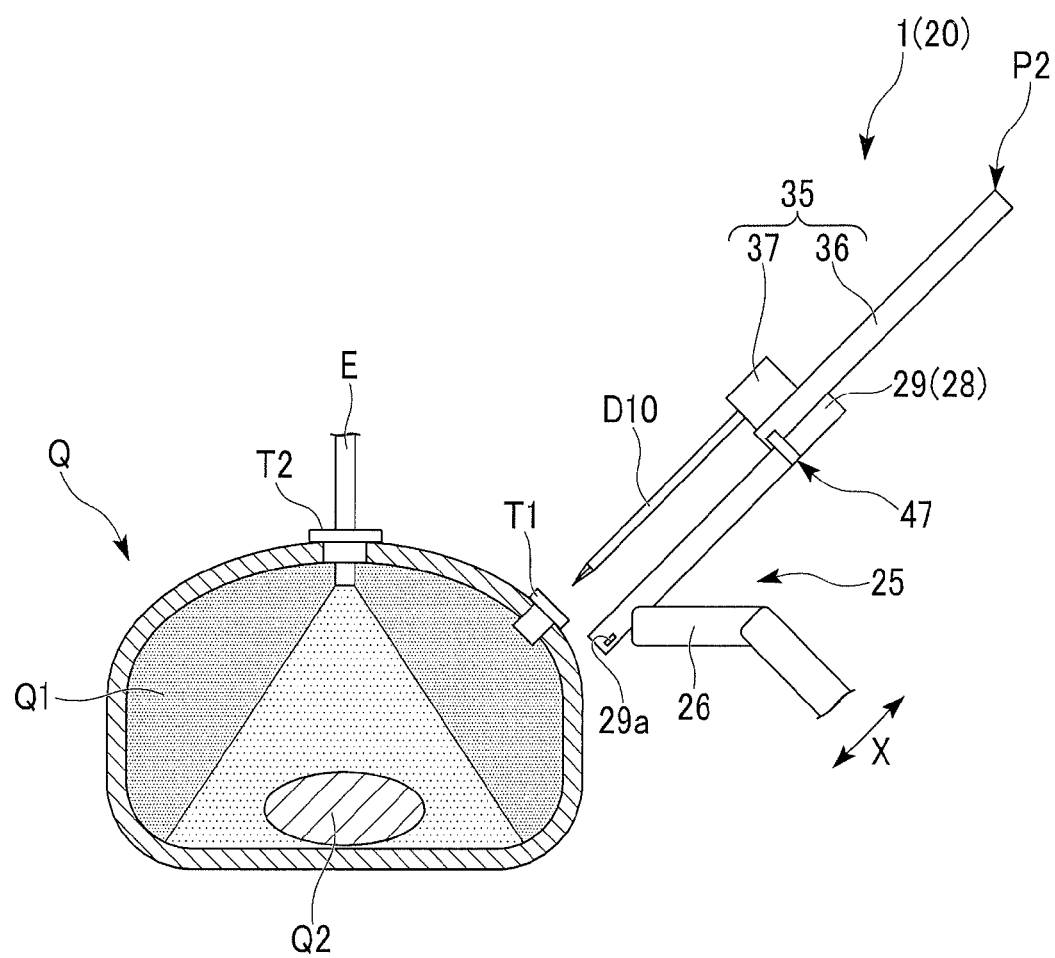
FIG. 8 is a schematic view for describing the procedure using the operation support apparatus according to the first embodiment of the present invention.

As shown in FIG. 8, the assistant manually moves the slide table 36 to the proximal end side in the reference direction X with respect to the base plate 28 to dispose the slide table 36 at the proximal end position P2. Then, the forceps D10 is extracted from the body cavity Q1 of the patient Q.

The claw 48 of the rotating claw unit 47 is engaged with the through-hole 29b, and the slide table 36 is fixed at the proximal end position P2 with respect to the base plate 28.

The forceps D10 is removed from the holding unit 37, and the high frequency incision tool D20 is attached to the holding unit 37.

The support member 49 is manipulated to release engagement of the through-hole 29b with the claw 48.

As shown in FIG. 9, the slide table 36 is manually moved to the distal end side in the reference direction X with respect to the base plate 28, and the high frequency incision tool D20 is introduced into the body cavity Q1 through the trocar T1. The slide table 36 is disposed on the distal end position P1, and the slide table 36 is fixed with respect to the base plate 28 by the rotating claw unit 47. As described above, before and after exchange of the treatment tool, the slide table 36 is disposed at the distal end position P1 with respect to the base plate 28.

The length L1 of the forceps D10 is set to be equal to the length L3 of the high frequency incision tool D20. For this reason, the cutting part D21 of the high frequency incision tool D20 can be disposed at substantially the same position as the position at which the treatment section D16 of the forceps D10 is disposed before exchange of the treatment tool.

The operator O manipulates the manipulation unit 11 to apply a high frequency voltage to the cutting part D21 to perform treatment such as incision of the target tissue Q2 or the like.

When the treatment by the high frequency incision tool D20 is finished, as the slide table 36 is moved to the proximal end side with respect to the base plate 28, the high frequency incision tool D20 is extracted from the body cavity Q1 through the trocar T1.

The endoscope apparatus E is extracted through the trocar T2, and the trocars T1 and T2 are removed from the patient Q. After that, an appropriate treatment such as suturing of the incision formed upon attachment of the trocars T1 and T2 to the patient Q, or the like, is performed to complete a series of surgeries.

As described above, according to the slave manipulator 20 of the present first embodiment, the slide table 36 is disposed at the distal end position P1 with respect to the base plate 28 of the slave arm 25, and the slide table 36 is positioned at the distal end position P1 with respect to the base plate 28 by the positioning mechanism 52. The holding unit 37 is moved to the proximal end side in the reference direction X with respect to the slide table 36 by the holding unit driving device 40. The forceps D10 is attached to the holding unit 37 such that the longitudinal direction of the forceps D10 is substantially parallel to the reference direction X.

As the holding unit 37 is moved to the distal end side in the reference direction X by the holding unit driving device 40 in a state in which the forceps D10 is held by the holding unit 37, the forceps D10 held to extend substantially parallel to the reference direction X can be easily introduced into the body cavity Q1 of the patient Q.

Further, upon exchange of the treatment tool, fixing of the slide table 36 with respect to the base plate 28 by the positioning mechanism 52 is released, and the assistant manually moves the slide table 36 and the holding unit 37 to the proximal end side in the reference direction X with respect to the base plate 28. Accordingly, the forceps D10 is moved with the holding unit 37 to the proximal end side in the reference direction X.

Release of the fixing by the positioning mechanism 52 and movement of the slide table 36 with respect to the base plate 28 are manually performed by the assistant. Accordingly, even when the slave control unit 60 or the like of the slave manipulator 20 electrically malfunctions and is inoperable, the forceps D10 can be rapidly extracted from the patient Q by mechanical manipulation.

Then, the forceps D10 is removed from the holding unit 37, and the high frequency incision tool D20 is attached to the holding unit 37. The slide table 36 and the holding unit 37 are manually moved to the distal end side in the reference direction X with respect to the base plate 28, and in a state in which the slide table 36 is disposed at the distal end position P1 with respect to the base plate 28, the slide table 36 is positioned with respect to the base plate 28 by the positioning mechanism 52.

Here, when the length L1 of the forceps D10 is set to be equal to the length L3 of the high frequency incision tool D20, the cutting part D21 of the high frequency incision tool D20 is disposed at substantially the same position as the position at which the treatment section D16 of the forceps D10 is disposed before exchange of the treatment tool. Accordingly, restarting of the treatment can be rapidly performed.

That is, unlike the conventional manipulator disclosed in U.S. Pat. No. 6,645,196, the distal end portion of the treatment tool after exchange with a mechanical mechanism can be disposed at the original treatment region without recording the dimension or disposition of the treatment tool in the recording unit. For this reason, the distal end portion of the treatment tool can be securely disposed using the mechanical manipulation only, without influence due to electrical malfunction of the slave control unit 60 or the like.

From the above, according to the present first embodiment, rapid exchange of the treatment tool with respect to the target tissue Q2 of the patient Q is possible.

The positioning mechanism 52 is configured by the through-holes 29a and 29b formed at the side plate 29, and the rotating claw unit 47. For this reason, the slide table 36 can be securely fixed in the reference direction X with respect to the base plate 28 with a simple configuration.

The rotating claw unit 47 is configured to bias the support member 49 rotatably supported around the rotating shaft 50 by the spring member 51. For the reason, a motion of the support member 49 supported by the rotating shaft 50 is stabilized.

Further, as the claw 48 is engaged with the through-hole 29b of the side plate 29, the slide table 36 can be fixed to the proximal end position P2 by the positioning mechanism 52. Accordingly, a task of exchanging the treatment tool with a new one at the proximal end position P2 can be securely performed in a state in which positions of the slide table 36 and the holding unit 37 are stable.

When the slide table 36 is moved to the proximal end side of the reference direction X with respect to the base plate 28, the slide table 36 can be removed from the base plate 28. For this reason, as the slide table 36 is moved to the proximal end side in the reference direction X with respect to the base plate 28 to be removed upon emergency or the like, the slide table 36 or the treatment tool can be rapidly and securely retracted from the patient Q.

In the present first embodiment, the rotating claw unit 47 is configured by the rotating shaft 50, the support member 49, and the spring member 51, which is a biasing member, which are configured by separate members. However, a rotating shaft, a support member, a claw, which is an engaged section, and a biasing member may be integrally formed of a resin or the like having elasticity, what is called, a rotating claw unit such as a snap fit may be installed.

In this case, the rotating shaft functions as the biasing member. For this reason, in a natural state in which the assistant does not apply a force, the rotating shaft biases the claw toward the through-hole 29a side through the support member such that the claw is engaged with the through-hole 29a. Then, as one end portion of the support member is manipulated to deform the rotating shaft such that the support member is rotated about the rotating shaft, engagement of the through-hole 29a and the claw is released.

In the present embodiment, the through-holes 29a and 29b are formed in the side plate 29 only. However, through-holes may be formed in a side plate 30 at positions opposite to the through-holes 29a and 29b, and a rotating claw unit engaged with the through-holes may be installed at the slide table 36.

Meanwhile, in the present embodiment, the through-hole 29b may not be formed in the side plate 29. In the proximal end position P2, since the treatment tool is extracted from the patient Q, the assistant may fix the slide table 36 with respect to the base plate 28.

Figure 10:
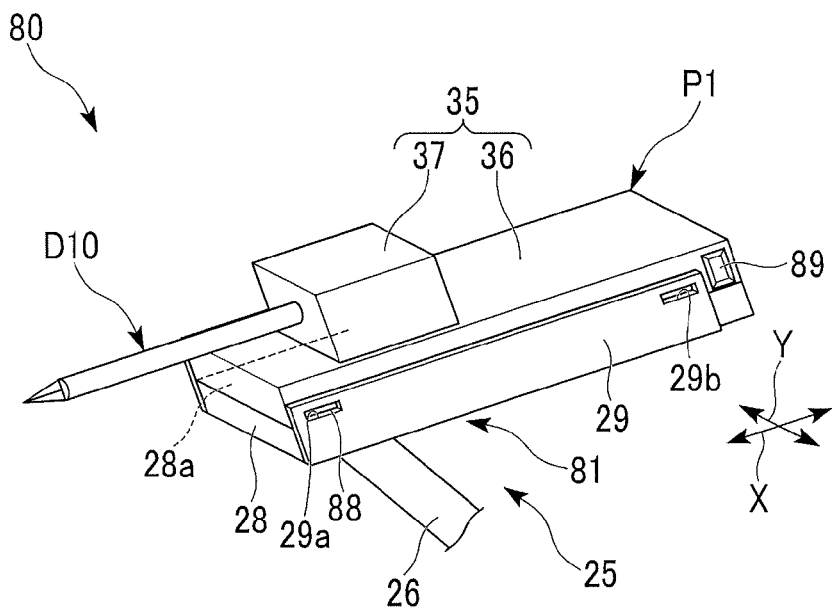
FIG. 10 is a perspective view of main parts of a medical manipulator according to a modified example of the first embodiment of the present invention.
Figure 11:
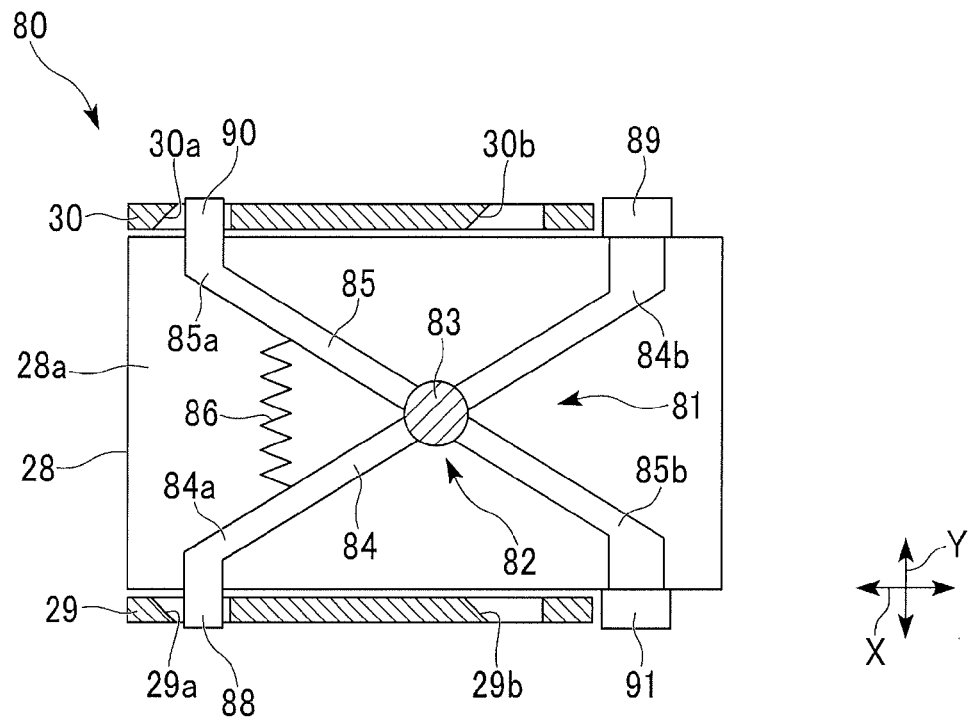
FIG. 11 is a plain cross-sectional view showing the medical manipulator according to the modified example of the first embodiment of the present invention in a state in which an assistant does not push a fixing release button.

In addition, in the present embodiment, like a slave manipulator 80 shown in FIGS. 10 and 11, instead of the positioning mechanism 52 of the first embodiment, a positioning mechanism 81 may be installed. The positioning mechanism 81 has through-holes 30a and 30b of the side plate 30, in addition to the through-holes 29a and 29b of the side plate 29 of the first embodiment, and a rotating claw unit 82.

The through-hole 30a of the side plate 30 is formed at a position opposite to the through-hole 29a of the side plate 29. More specifically, provided that a direction parallel to a support surface 28a and perpendicular to the reference direction X is referred to as a perpendicular direction Y, the through-hole 30a of the side plate 29 is formed at a position separated from the through-hole 29a in the perpendicular direction Y. Similarly, the through-hole 30b of the side plate 30 is formed at a position opposite to the through-hole 29b of the side plate 29.

The rotating claw unit 82 has rod-shaped link members (support members) 84 and 85 rotatably supported about a pin (a rotating shaft) 83 installed at the slide table 36, and spring members (a biasing member) 86 attached to the link members 84 and 85. The link members 84 and 85 are supported by the pin 83 at center portions in an extension direction in which the link members 84 and 85 extend. As well, one rotating claw unit is configured of the pin 83, the link member 84 and the spring member 86, and the other claw unit is configured of the pin 83, the link member 85 and the spring member 86. That is, the rotating claw unit 82 is configured of two rotating claw units. The two rotating claw units is configured to include the pin 83 and the spring member 86.

The link member 84 has one end portion (a first end portion) 84a disposed at the distal end side in the reference direction X with respect to the pin 83, and the other end portion (a second end portion) 84b disposed at the proximal end side in the reference direction X with respect to the pin 83. Similarly, the link member 85 has one end portion (a first end portion) 85a disposed at the distal end side in the reference direction X with respect to the pin 83, and the other end portion (a second end portion) 85b disposed at the proximal end side in the reference direction X with respect to the pin 83.

In this example, the spring members 86 are attached to the distal end portions in the reference direction X of the link members 84 and 85, respectively. Then, the spring member 86 biases the one end portion 84a of the link member 84 and the one end portion 85a of the link member 85 to make the one end portion 84a of the link member 84 and the one end portion 85a of the link member 85 being separated from each other. The link members 84 and 85 having the above-mentioned configuration are disposed to form an X shape when seen from a plan view.

A fixing section (an engaged section) 88 substantially parallel to the perpendicular direction Y and protruding in a direction which is outside with respect to the link members 84 and 85 is formed at the one end portion 84a of the link member 84. The fixing section 88 is formed to a size that can be engaged with the through-holes 29a and 29b of the side plate 29. When the fixing section 88 is engaged with the through-holes 29a and 29b, the fixing section 88 cannot be moved in the reference direction X with respect to the through-holes 29a and 29b. For this reason, movement of the slide table 36 in the reference direction X with respect to the base plate 28 is restricted. The fixing section 88 is configured to be disposed between the side plates 29 and 30 by rotating the link member 84.

A fixing release button 89 substantially parallel to the perpendicular direction Y and protruding in a direction which is outside with respect to the link members 84 and 85 is formed at the other end portion 84b of the link member 84.

In the link member 85, similar to the link member 84, a fixing section (an engaged section) 90 is formed at the one end portion 85a, and a fixing release button 91 is formed at the other end portion 85b.

The fixing release buttons 89 and 91 are disposed at the proximal end side in the reference direction X of the slide table 36. Furthermore, the fixing release buttons 89 and 91 are disposed to protrude in the perpendicular direction Y with respect to the base plate 28 and the slide table 36.

Figure 12:
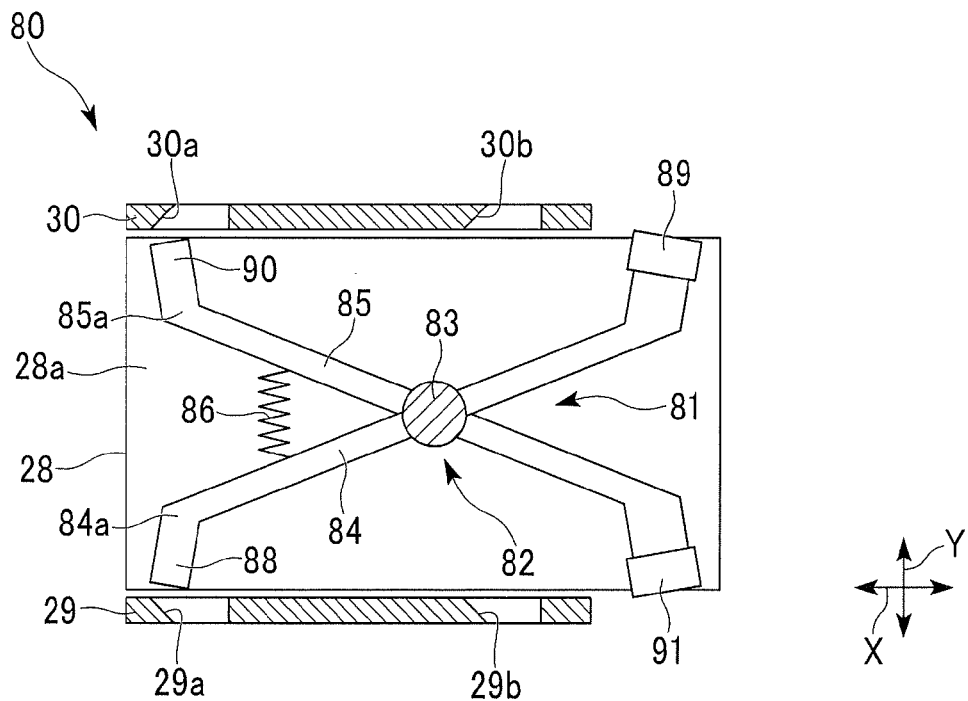
FIG. 12 is a plain cross-sectional view showing the medical manipulator according to the variant of the first embodiment of the present invention in a state in which the assistant pushes the fixing release button.

In the slave manipulator 80 having the above-mentioned configuration, as shown in FIG. 12, the assistant pushes the fixing release buttons 89 and 91 such that the fixing release buttons 89 and 91 approach each other in the perpendicular direction Y against the biasing force of the spring member 86, the link members 84 and 85 rotate about the pin 83. Accordingly, the one end portions 84*a* and 85*a* approach each other to release engagement between the through-hole 29*a* and the fixing section 88 and between the through-hole 30*a* and the fixing section 90. As a result, the slide table 36 can be moved in the reference direction X with respect to the base plate 28.

In addition, when the slide table 36 is moved to the proximal end side in the reference direction X with respect to the base plate 28 to dispose the slide table 36 at the proximal end position P2, the fixing sections 88 and 90 are engaged with the through-holes 29*b* and 30*b*, respectively, so that the slide table 36 is fixed to the proximal end position P2.

According to the slave manipulator 80 of the present modified example, the positioning mechanism 81 includes the pair of rotating claws, that is, the pair of link members 84 and 85. For this reason, even when one of the fixing release buttons 89 and 91 is pushed, engagement of the base plate 28 with the slide table 36 is not perfectly released. For this reason, release of the engagement of the base plate 28 with the slide table 36 due to unintentional contact of the assistant with the fixing release buttons 89 and 91 can be suppressed.

Further, the fixing release buttons 89 and 91 are disposed at the proximal end side in the reference direction X of the slide table 36. For this reason, manipulation of fixing of the slide table 36 to the base plate 28 or manipulation of releasing the fixing of the base plate 28 and the slide table 36 are performed by one hand of the assistant, without interference due to the treatment tool such as the holding unit 37, the forceps D10 or the like. Accordingly, manipulation performance of the slave manipulator 80 is improved.

In addition, in the present modified example, the spring member 86 is attached to the distal end portions in the reference direction X of the link members 84 and 85. However, the spring member 86 may be attached to the proximal end portions in the reference direction X of the link members 84 and 85.

In the present modified example, the slave manipulator 80 may not include the link member 85 and the through-holes 30*a* and 30*b* of the side plate 30. Even when the above-mentioned configurations are not provided, the slide table 36 can be fixed at the distal end position P1 and the proximal end position P2 with respect to the base plate 28 using the link member 84 and the through-holes 29*a* and 29*b* of the side plate 29.

Second Embodiment

Next, the second embodiment of the present invention will be described with reference to FIGS. 13 and 14. Like reference numerals in the embodiments designate like elements and description thereof will be omitted, and the second embodiment will be described focusing on differences from the first embodiment.

Figure 13:
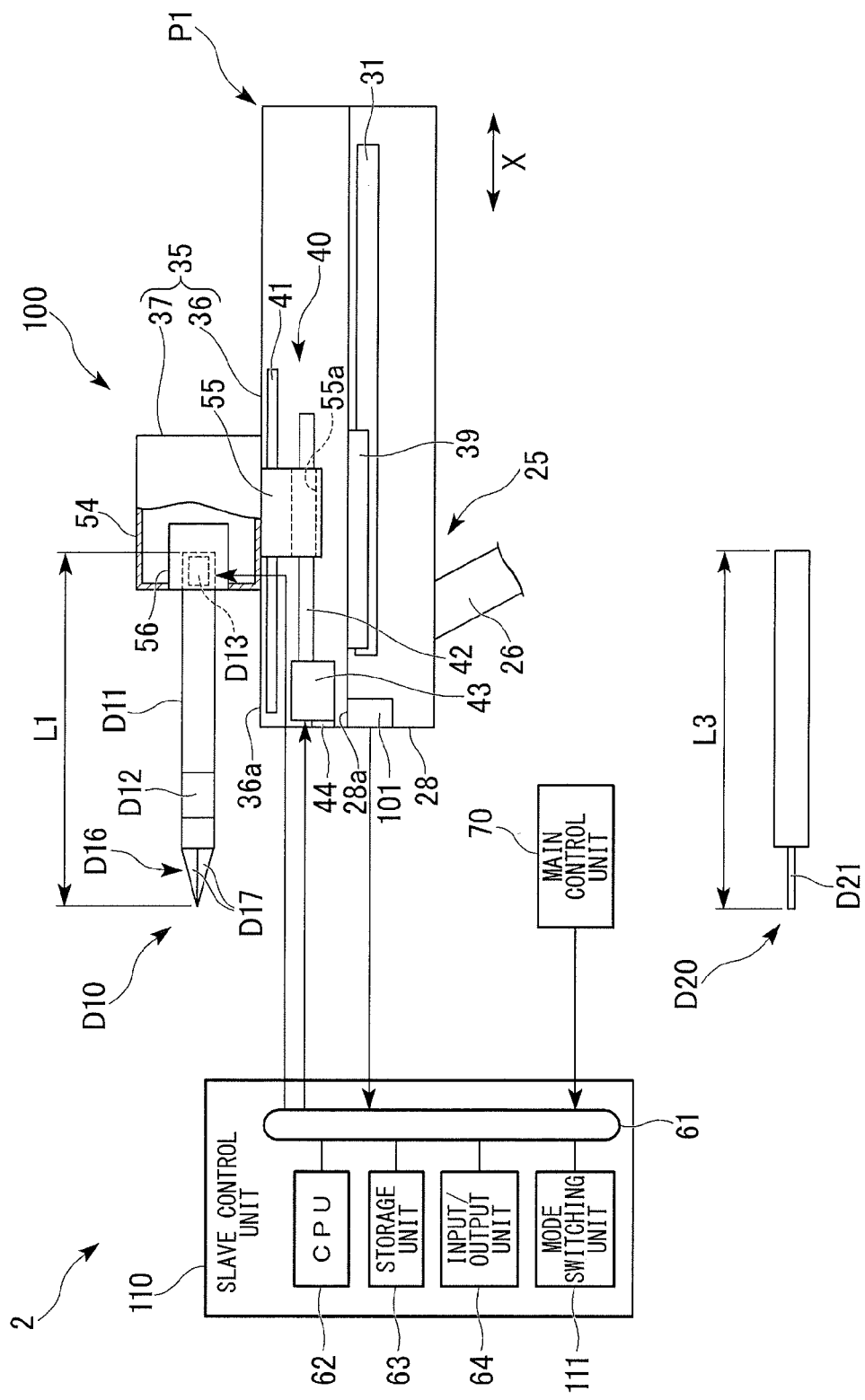
FIG. 13 is a view schematically showing a configuration of main parts of a medical manipulator according to a second embodiment of the present invention.
Figure 14:
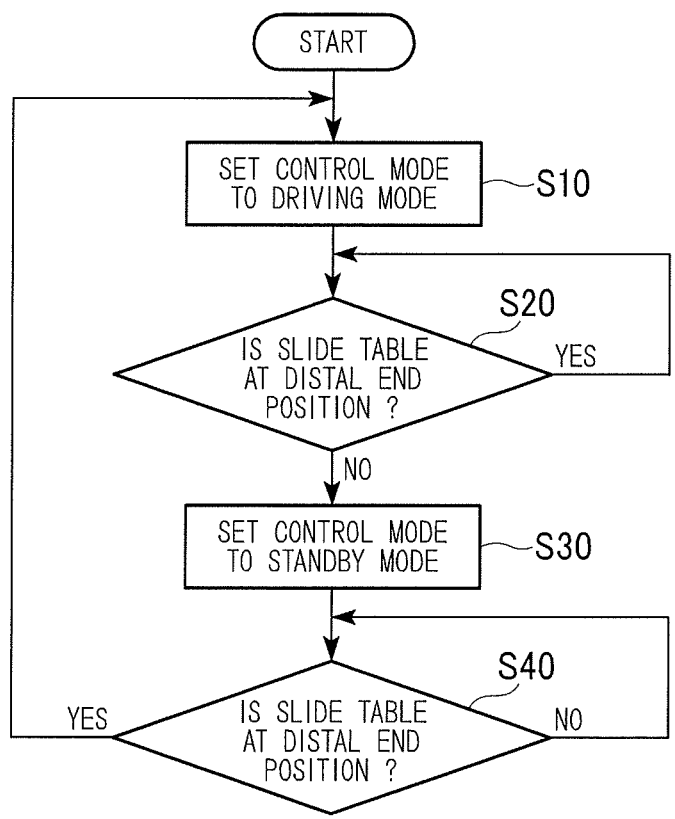
FIG. 14 is a flowchart showing a switching process of a control mode of a slave control unit of the medical manipulator according to the second embodiment of the present invention.

As shown in FIG. 13, a slave manipulator 100 used in an operation support apparatus 2 includes a position detecting unit 101 in the base plate 28, and includes a slave control unit (a control unit) 110 instead of the slave control unit 60, in the slave manipulator 20 of the first embodiment.

The position detecting unit 101 has a well-known proximity sensor (not shown) and a determination board connected to the proximity sensor. The position detecting unit 101 is disposed at the distal end portion in the reference direction X in the base plate 28. When the slide table 36 is disposed at the distal end position P1 with respect to the base plate 28, for example, electric field distribution is varied by the base plate 28 made of a metal. The proximity sensor detects variation in electric field distribution as a voltage value. The determination board can compare the detected voltage value with a predetermined threshold to detect whether the slide table 36 is in a distal end disposition state in which the slide table 36 is disposed at the distal end position P1 or a non-distal end disposition state in which the slide table 36 is not disposed at the distal end position P1 with respect to the base plate 28.

The position detecting unit 101 is connected to a bus 61 of the slave control unit 110. The position detecting unit 101 outputs a detection result of the distal end disposition state or the non-distal end disposition state to a mode switching unit 111 described later via the bus 61.

The slave control unit 110 includes the mode switching unit 111 in addition to each configuration of the slave control unit 60 of the first embodiment. The mode switching unit 111 can switch a control mode, in which the CPU 62 drives the servo motor 43, between a driving mode and a standby mode, based on the detection result transmitted from the position detecting unit 101.

The driving mode is a control mode of controlling movement in the reference direction X of the slide table 36 by the servo motor 43 based on a manipulation signal output from the manipulation unit 11. Meanwhile, the standby mode is a control mode of not controlling the servo motor 43 regardless of the output manipulation signal. Then, the mode switching unit 111 sets the control mode to the driving mode when the detection result transmitted from the position detecting unit 101 is the distal end disposition state, and sets the control mode to the standby mode when the detection result is the non-distal end disposition state.

For example, the mode switching unit 111 sets the control mode to the driving mode or the standby mode according to a control procedure to be described below.

The mode switching unit 111 has a memory (not shown). A flag corresponding to the driving mode and the standby mode is stored in the memory. The CPU 62 periodically reads the flag from the memory of the mode switching unit 111 according to predetermined readout timing. Then, the CPU 62 controls the servo motor 43 according to the read flag.

Using the above-mentioned control procedure, the control mode in which the CPU 62 controls the servo motor 43 is switched between the driving mode and the standby mode based on a disposition state detected by the position detecting unit 101.

Next, in the operation support apparatus 2 having the above-mentioned configuration, a process of switching the control mode will be described. FIG. 14 is a flowchart showing a process of switching the control mode of the slave control unit 110.

Hereinafter, the process will be described based on a premise in which the slide table 36 is previously disposed at the distal end position P1 with respect to the base plate 28.

When the operation support apparatus 2 is started, power is supplied to the slave manipulator 20.

First, in step S10, the control mode is set to the driving mode. Specifically, the detection result showing the distal end disposition state is output from the position detecting unit 101 to the mode switching unit 111. In the mode switching unit 111, the flag corresponding to the driving mode is stored in the memory.

Next, after the readout timing from the beginning of step S10, in step S20, the position detecting unit 101 determines whether the slide table 36 is disposed at the distal end position P1 or not.

When the position detecting unit 101 detects that the slide table 36 is disposed at the distal end position P1 (YES), step S20 is performed again. That is, while the slide table 36 is disposed at the distal end position P1, movement of the slide table 36 in the reference direction X by the servo motor 43 is controlled based on a manipulation signal output from the manipulation unit 11.

Meanwhile, in step S20, when the position detecting unit 101 detects that the slide table 36 is not disposed at the distal end position P1 (NO), step S30 is performed. For example, when the assistant manually moves the slide table 36 from the distal end position P1 to the proximal end position P2 with respect to the base plate 28 or while moving the slide table 36 from the distal end position P1 to the proximal end position P2, it is detected that the slide table 36 is not disposed at the distal end position P1 in step S20.

In step S30, the control mode is set to the standby mode. Specifically, the detection result showing the non-distal end disposition state is output from the position detecting unit 101 to the mode switching unit 111. In the mode switching unit 111, the flag corresponding to the standby mode is stored in the memory, and step S40 is performed.

In step S40, after the readout timing from the beginning of step S20, the position detecting unit 101 determines whether the slide table 36 is disposed at the distal end position P1 or not.

When the position detecting unit 101 detects that the slide table 36 is disposed at the distal end position P1 (YES), step S10 is performed. For example, when the assistant manually returns the slide table 36 to the distal end position P1 with respect to the base plate 28, it is detected that the slide table 36 is disposed at the distal end position P1 in step S40.

Meanwhile, in step S40, when the position detecting unit 101 detects that the slide table 36 is not disposed at the distal end position P1 (NO), step S40 is performed again. That is, while the slide table 36 is not disposed at the distal end position P1, the servo motor 43 is not controlled regardless of the output manipulation signal.

As described above, at every readout timing, the position detecting unit 101 detects whether the slide table 36 is disposed at the distal end position P1 or not, and the control mode is switched between the driving mode and the standby mode based on the detection result.

The process is continued until the operation support apparatus 2 is stopped.

As described above, according to the slave manipulator 100 of the second embodiment, even when the control device electrically malfunctions, the treatment tool can be rapidly extracted from the patient Q.

Further, when the slide table 36 is not disposed at the distal end position P1, the control mode is set to the standby mode such that control of the servo motor 43 is not performed regardless of the manipulation signal output from the manipulation unit 11. Accordingly, in the middle of movement of the slide table 36 from the distal end position P1 and exchange of the treatment tool, movement of the holding unit 37 with respect to the slide table 36 due to an operational error of the manipulation unit 11 can be prevented.

Furthermore, upon exchange of the treatment tool, a position of the holding unit 37 with respect to the slide table 36 can be defined. For this reason, when the lengths of the treatment tools are equal, the distal end position of the treatment tool after the exchange can be returned to the original distal end position without recording the distal end position of the treatment tool before the exchange.

In addition, in the present second embodiment, the proximity sensor is used to detect a position of the base plate 28 in the position detecting unit 101. However, a sensor used in the position detecting unit 101 is not limited to the proximity sensor. A micro-switch, a photoelectric sensor, a magnetic sensor, or the like can be appropriately selected and used as long as a member can detect a position of the base plate 28.

Further, a configuration of switching the control mode between the driving mode and the standby mode with respect to a plurality of sets of a slave arm 25 and a movable holding section 35 included in the slave manipulator 100 may be provided. That is, the control mode may be switched to the standby mode by only a set of the slave arm 25 and the movable holding section 35, which is needed for exchange of the treatment tool, and the control mode of the other sets may maintain the driving mode to perform the manipulation using the manipulation unit 11.

In the present second embodiment, in the standby mode, the CPU 62 is configured not to drive the servo motor 43. However, in the present second embodiment, in the standby mode, the CPU 62 is configured not to drive the driving unit D13. In this case, when the curved section D12 of the forceps D10 is bent and used as described in the first embodiment, the CPU 62 may be configured not to drive the servo motor 43 and the driving unit D13 after the curved section D12 is straightened.

As the curved section D12 is in a straight state, the forceps D10 can be easily extracted from the patient Q.

Third Embodiment

Next, the third embodiment of the present invention will be described with respect to FIGS. 15 and 16. Like reference numerals in the embodiments designate like elements and description thereof will be omitted, and the third embodiment will be described focusing on differences from the above-mentioned embodiments.

Figure 15:
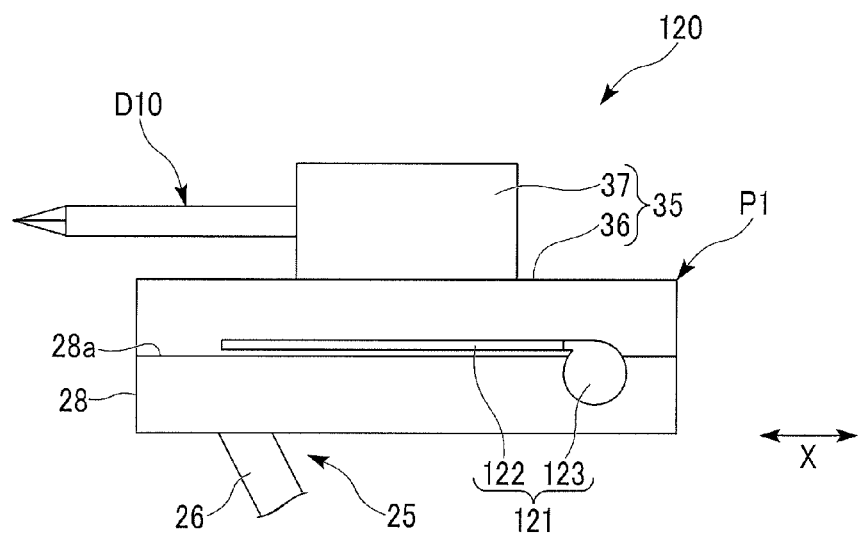
FIG. 15 is a view schematically showing a configuration of main parts of a medical manipulator according to a third embodiment of the present invention in a state in which a slide table is disposed at a distal end position.
Figure 16:
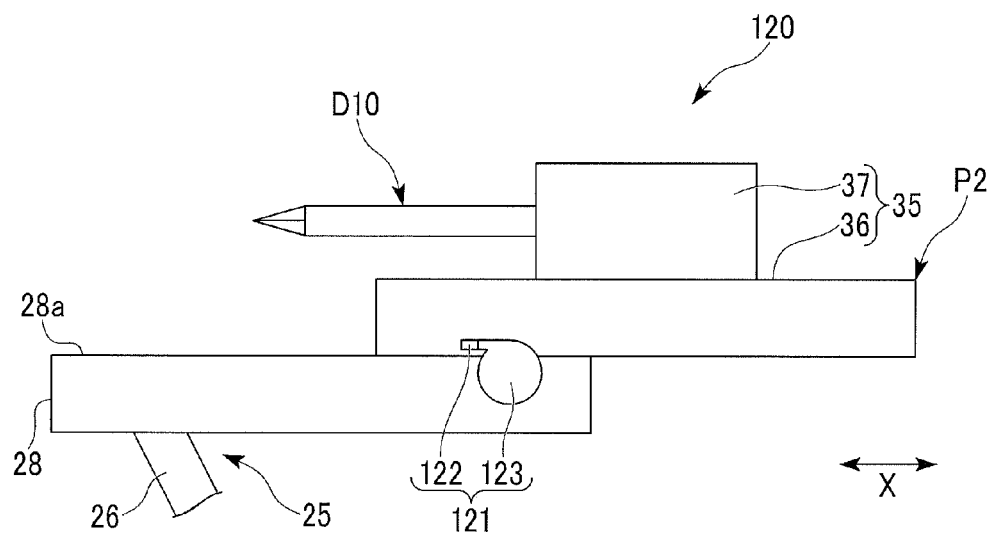
FIG. 16 is a view schematically showing a configuration of main parts of the medical manipulator according to the third embodiment of the present invention in a state in which the slide table is disposed at a proximal end position.

As shown in FIG. 15, a slave manipulator 120 of the present third embodiment includes a biasing mechanism 121 for biasing the slide table 36 to the proximal end side in the reference direction X with respect to the base plate 28, in addition to each element of the slave manipulator 20 of the first embodiment.

In the present third embodiment, as the biasing mechanism 121, for example, a constant load spring 122 such as Constonn (Registered Trademark, manufactured by Sunco Spring Co., Ltd) or the like is housed in a reel 123. In the reel 123, a drum (not shown) turnably supported by the reel 123 is provided. The proximal end portion of the constant load spring 122 is attached to the drum and wound around the drum.

The reel 123 is fixed to the proximal end portion in the reference direction X of the base plate 28 such that a direction of pulling the constant load spring 122 from the inside of the reel 123 becomes the distal end side in the reference direction X. The distal end portion of the constant load spring 122 is fixed to the distal end portion in the reference direction X of the slide table 36.

As the constant load spring 122 is used, a biasing force (a load) by which the biasing mechanism 121 biases the slide table 36 with respect to the base plate 28 is constant regardless of the position of the slide table 36 in the reference direction X with respect to the base plate 28.

The biasing force of the biasing mechanism 121 may be appropriately set. The biasing force of the biasing mechanism 121 is preferably set, for example, in consideration of a maximum inclination angle of the top surface 28a with respect to a horizontal surface when the top surface 28a is inclined from the horizontal surface and used.

As one of the methods of setting the biasing force, there is a method of setting an element parallel to the top surface 28a, among gravity applied to the slide table 36, the holding unit 37 and treatment tool (hereinafter referred to as "the slide table 36 or the like"), to be substantially equal to the biasing force when the top surface 28a is disposed to form the maximum inclination angle with respect to the horizontal surface.

According to the method, the slide table 36 can be maintained at an arbitrary position in the reference direction X with respect to the base plate 28. For this reason, the biasing mechanism 121 functions as a gravity compensation of the slide table 36 or the like. Accordingly, when the fixing of the base plate 28 and the slide table 36 is released by the positioning mechanism 52, unintentional movement of the slide table 36 can be prevented.

Further, as another one of the methods of setting the biasing force, there is a method of setting the biasing force to be larger than an element parallel to the top surface 28a, among the gravity. According to the method, when the assistant or the like releases his/her grip from the slide table 36, the slide table 36 can be automatically moved to the proximal end side in the reference direction X with respect to the base plate 28 as shown in FIG. 16, and the treatment tool such as the forceps D10 or the like can be automatically separated from the patient Q.

In addition, as the slave manipulator 120 includes the biasing mechanism 121, even when the slide table 36 is moved to the proximal end side in the reference direction X with respect to the base plate 28, the biasing mechanism 121 becomes an obstacle, and thus, the slide table 36 cannot be removed from the base plate 28.

According to the slave manipulator 100 of the present third embodiment having the above-mentioned configuration, even when the control device electrically malfunctions, the treatment tool can be rapidly extracted from the patient Q.

Furthermore, as the biasing mechanism 121 is provided, unintentional movement of the slide table 36 to the distal end side in the reference direction X with respect to the base plate 28 can be suppressed.

When the top surface 28a is inclined with respect to the horizontal surface, and an element parallel to the top surface 28a among the gravity applied to the slide table 36 or the like is substantially equal to the biasing force of the biasing mechanism 121, the slide table 36 can be maintained at an arbitrary position in the reference direction X with respect to the base plate 28. Since the biasing force of the biasing mechanism 121 is constant regardless of the position in the reference direction X of the slide table 36, manipulation performance upon manipulation of the slide table 36 by the assistant can be improved.

In addition, in the present third embodiment, instead of the biasing mechanism 121 using the constant load spring 122, as the biasing mechanism, a helical spring or an electric motor that can move the slide table 36 in the reference direction X with respect to the base plate 28 may be used. In the mechanism using the electric motor, the slide table 36 may also be manually moved in the reference direction X.

Even in this case, in order to restrict the fixing position of the slide table 36, the treatment tool distal end position after the exchange can be set to the distal end position before the exchange. For this reason, the treatment tool can be rapidly exchanged with a new one.

While the first to third embodiments of the present invention have been described with reference to the accompanying drawings, specific configurations are not limited to the present embodiments but may include modifications or the like without departing from the spirit of the present invention. Furthermore, it is needless to say that configurations described in the present embodiments may be appropriately combined and used.

For example, in the first to third embodiments, the length L1 of the forceps D10 is equal to the length L3 in the longitudinal direction of the high frequency incision tool D20. However, these lengths may differ. When the length L1 of the forceps D10 is set to be smaller than a length between the distal end position P1 of the slide table 36 and the proximal end position P2 of the slide table 36, the forceps D10 can be rapidly extracted from the patient Q.

In addition, in case in which the length L1 of the forceps D10 is set to be larger than the length L3 of the high frequency incision tool D20, the treatment is operated as described below. That is, as the holding unit driving device 40 is previously driven before the forceps D10 is retracted from the body, the distal end portion of the forceps D10 are separated from the treated tissue in the body more than a value calculated by an equation (L3−L1) which is a difference between the length of the forceps D10 and the high frequency incision tool D20. As a result, the distal end of the high frequency incision tool D20 after exchange does not contact with the treated tissue in the body, and the distal end of the high frequency incision tool D20 can be disposed in the treatment region.

In addition, in the first to third embodiments, the length L1 of the forceps D10 is set to be smaller than the length L2 between the distal end position P1 of the slide table 36 and the proximal end position P2 of the slide table 36 in the reference direction X. However, the length L1 of the forceps D10 may be set to be longer than the length L2 between the distal end position P1 of the slide table 36 and the proximal end position P2 of the slide table 36 in the reference direction X.

In this case, the base plate 28 and the trocar are installed such that the base plate 28 is separated from the trocar more than a value calculated by an equation (L1−L2) which is a difference between the distal end position P1 of the slide table 36 and the proximal end position P2 of the slide table 36 in the reference direction X. As a result, the forceps D10 can be extracted from the patient.

Figure 17:
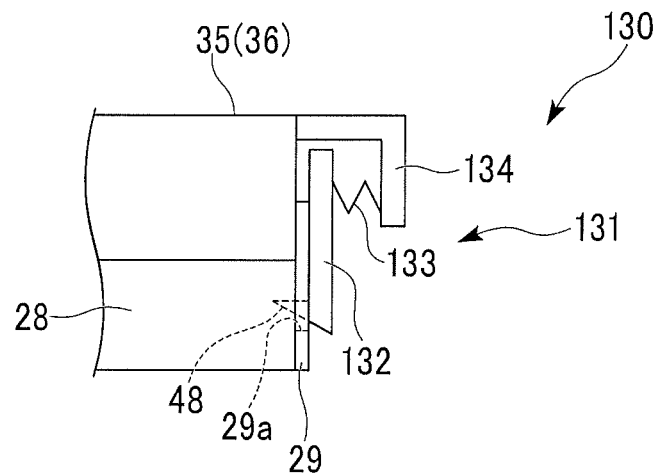
FIG. 17 is a front view of main parts of a slave arm and a movable holding section of a medical manipulator according to a modified example of the present invention.

In the first to third embodiments, as shown in FIG. 17, instead of the rotating claw unit 47 of the positioning mechanism 52 of the present embodiment, a positioning mechanism 130 including a moving claw section (an engaged device) 131 may be provided.

In the present modified example, the moving claw section 131 has a support member 132 in which the claw 48 is formed at one end portion thereof, and a spring member 133 configured to bias the other end portion of the support member 132 such that the claw 48 is engaged with the through-holes 29a and 29b. The claw 48 is formed at a surface of one end portion of the support member 132 in the side plate 29 side. The spring member 133 is installed at the slide table 36. The spring member 133 is connected to a connecting member 134 having an L shape when seen in the reference direction X in parallel and the other end portion of the support member 132.

In a natural state in which the assistant does not apply a force to the support member 132, as the spring member 133 biases the support member 132 toward the side plate 29 side, engagement of the claw 48 with the through-hole 29a is maintained. Accordingly, movement of the slide table 36 in the reference direction X with respect to the base plate 28 is restricted.

Figure 18:
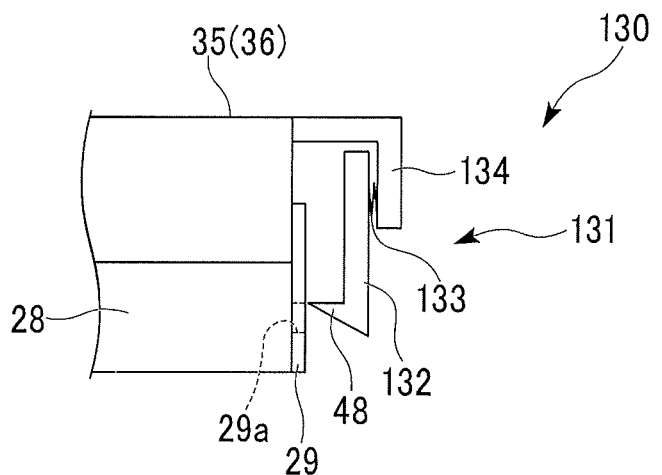
FIG. 18 is a front view of the main parts of the slave arm and the movable holding section according to the variant of the present invention in a state in which engagement of a through-hole and a claw is released.

Meanwhile, as the assistant grips the support member 132 and pulls (moves in parallel) the support member 132 to be separated from the slide table 36 against a biasing force of a spring member 133 as shown in FIG. 18, engagement of the through-hole 29a with the claw 48 is released. Accordingly, the slide table 36 can be moved in the reference direction X with respect to the base plate 28.

In addition, in the first to third embodiments and the present modified example, as the biasing member, the spring member is used, but the biasing member is not limited to the spring member. As the biasing member, for example, a magnet may be used. Specifically, a support member side magnet is installed to the other end portion of the support member 49 such that north pole thereof orients to a side of the slide table 36, and a table side magnet is installed to the slide table 36 such that the north pole thereof orients to the other end side of the support member 49. As the support member side magnet and the table side magnet repel, bias force is generated such that the claw 48 engages with the through-hole 29a.

In the present modified example, poles of the support member side magnet and the table side magnet facing each other may be set to be a south pole.

In the first to third embodiments, the through-hole 29a is formed in the slave arm 25 as the engaging section, and the claw 48 is installed at the slide table 36 as the engaged section. However, the claw may be installed at the slave arm 25 as the engaging section, and the through-hole engaged with the claw may be formed in the slide table 36 as the engaged section. Further, the claw may be installed at the support member rotatably supported about the rotating shaft of the slave arm 25 as the engaged section, and the through-hole engaged with the claw may be formed in the slide table 36 as the engaging section.

Further, the slave arm 25 having the movable joint section 27 is installed as the base section. However, the base section is not limited to this configuration but may be configured by a simple support with no movable part.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A medical manipulator comprising:
a base section at which a support surface is formed;
a movable part movably supported on the support surface, between a distal end position, which is a distal end side in a reference direction, and a proximal end position, which is a proximal end side in the reference direction, with respect to the base section, when the reference direction parallel to the support surface is defined;
a positioning mechanism configured to position the movable part at the distal end position with respect to the base section;
a holding section movably supported in the reference direction with respect to the movable part, and configured to detachably hold a proximal end portion of a treatment tool such that a longitudinal direction of the treatment tool having an elongated shape is substantially parallel to the reference direction; and
a driving unit configured to move the holding section in the reference direction with respect to the movable part,
wherein the positioning mechanism includes:
an engaging section provided at one of the base section and the movable part; and
an engaged device having an engaged section provided at an other of the base section and the movable part, and restricted movement to the reference direction on engaging with the engaging section, and
wherein the engaged device includes:
a support member configured to support the engaged section; and
a biasing member configured to bias the support member such that the engaged section engages with the engaging section.

2. The medical manipulator according to claim 1, wherein the engaged device includes a rotating shaft configured to rotatably connect the other of the base section and the movable part to the support member, and
the biasing member biases the support member to rotate about the rotating shaft.

3. The medical manipulator according to claim 2, wherein the support member has a rod shape;
the support member is supported by the rotating shaft at an intermediate section in an extension direction in which the support member extends;
the engaged section is provided at a first end portion of the support member, which is a distal end side in the reference direction, and
a second end portion of the support member is disposed at the proximal end side in the reference direction with respect to the first end portion of the support member.

4. The medical manipulator according to claim 3, wherein the positioning mechanism includes a pair of engaging sections and a pair of engaged devices;
the pair of engaging sections are provided so as to separate from each other in a perpendicular direction perpendicular to the reference direction parallel to the support surface;
the engaged sections of the engaged devices are configured to be disposed between the pair of engaging sections, and
the biasing member biases the first end portions of the support members to make the first end portions of the support members being separated from each other.

5. The medical manipulator according to claim 1, wherein the positioning mechanism positions the movable part at the proximal end position with respect to the base section.

6. The medical manipulator according to claim 1, wherein, when the movable part is moved to the proximal end side in the reference direction with respect to the base section, the movable part can be removed from the base section.

7. The medical manipulator according to claim 1, wherein a length in a longitudinal direction of the treatment tool is set to be smaller than a length in the reference direction between the distal end position and the proximal end position.

8. The medical manipulator according to claim 1, wherein lengths in the longitudinal direction of a plurality of treatment tools detachably held by the holding section are equal to each other.

9. A medical manipulator comprising:
a base section at which a support surface is formed;
a movable part movably supported on the support surface, between a distal end position, which is a distal end side in a reference direction, and a proximal end position, which is a proximal end side in the reference direction, with respect to the base section, when the reference direction parallel to the support surface is defined;
a positioning mechanism configured to position the movable part at the distal end position with respect to the base section;
a holding section movably supported in the reference direction with respect to the movable part, and configured to detachably hold a proximal end portion of a treatment tool such that a longitudinal direction of the treatment tool having an elongated shape is substantially parallel to the reference direction;
a driving unit configured to move the holding section in the reference direction with respect to the movable part,
a position detecting unit configured to detect a distal end disposition state in which the movable part is disposed at the distal end position with respect to the base section or a non-distal end disposition state in which the movable part is not disposed at the distal end position with respect to the base section;
an input unit configured to output a manipulation signal to control the driving unit based on an input from an operator; and
a control unit having a driving mode of controlling movement in the reference direction of the holding section by the driving unit and a standby mode of not controlling the driving unit based on the manipulation signal, and configured to select the driving mode when the position detecting unit detects the distal end disposition state and the standby mode when the position detecting unit detects the non-distal end disposition state.

10. A medical manipulator comprising:
a base section at which a support surface is formed;
a movable part movably supported on the support surface, between a distal end position, which is a distal end side in a reference direction, and a proximal end position, which is a proximal end side in the reference direction, with respect to the base section, when the reference direction parallel to the support surface is defined;
a positioning mechanism configured to position the movable part at the distal end position with respect to the base section;
a holding section movably supported in the reference direction with respect to the movable part, and configured to detachably hold a proximal end portion of a treatment tool such that a longitudinal direction of the treatment tool having an elongated shape is substantially parallel to the reference direction;
a driving unit configured to move the holding section in the reference direction with respect to the movable part, and
a biasing mechanism configured to bias the movable part to the proximal end side in the reference direction with respect to the base section.

11. The medical manipulator according to claim 10, wherein a biasing force applied to bias the movable part by the biasing mechanism is constant regardless of a position of the movable part in the reference direction with respect to the base section.

* * * * *